United States Patent
Gamarino et al.

(10) Patent No.: US 9,447,477 B2
(45) Date of Patent: Sep. 20, 2016

(54) FAT-LIQUORING

(71) Applicant: Stahl International B.V., Waalwijk (NL)

(72) Inventors: Roberta Gamarino, Casale Monferrato (IT); Licia Trimarco, Saronno (IT); Maurizio Quaglierini, Chianni (IT); Claus Reineking, Waldenbuch (DE)

(73) Assignee: STAHL INTERNATIONAL B.V., Waalwijk (NL)

( * ) Notice: Subject to any disclaimer, the term of this patent is extended or adjusted under 35 U.S.C. 154(b) by 158 days.

(21) Appl. No.: 14/374,867

(22) PCT Filed: Jan. 3, 2013

(86) PCT No.: PCT/EP2013/000009
§ 371 (c)(1),
(2) Date: Jul. 25, 2014

(87) PCT Pub. No.: WO2013/110428
PCT Pub. Date: Aug. 1, 2013

(65) Prior Publication Data
US 2014/0366280 A1    Dec. 18, 2014

(51) Int. Cl.
*C14C 9/02* (2006.01)
*C14C 3/28* (2006.01)
*C14C 9/00* (2006.01)
*C08G 77/26* (2006.01)
*C08G 77/388* (2006.01)
*C07F 7/08* (2006.01)

(52) U.S. Cl.
CPC .............. *C14C 3/28* (2013.01); *C07F 7/0859* (2013.01); *C07F 7/0874* (2013.01); *C08G 77/26* (2013.01); *C08G 77/388* (2013.01); *C14C 9/00* (2013.01)

(58) Field of Classification Search
CPC .......... C14C 9/00; C14C 3/28; C08G 77/26; C08G 77/288; C07F 7/0859; C07F 7/0874
USPC ...................................................... 8/94.19 R
See application file for complete search history.

(56) References Cited

U.S. PATENT DOCUMENTS

| 5,686,011 | A | 11/1997 | Lohmann et al. |
| 6,110,230 | A | 8/2000 | Friedrich et al. |
| 7,652,120 | B2 * | 1/2010 | Danner ............... C08G 77/388 524/838 |
| 2007/0212319 | A1 | 9/2007 | Otterson et al. |

FOREIGN PATENT DOCUMENTS

| DE | 19707970 A1 | 9/1998 |
| EP | 0283156 A2 | 9/1988 |

OTHER PUBLICATIONS

STIC Search Report dated Feb. 29, 2016.*
International Search Report dated Jun. 12, 2013 for PCT/EP2013/000009.

* cited by examiner

*Primary Examiner* — Eisa Elhilo
(74) *Attorney, Agent, or Firm* — Knobbe, Martens, Olson & Bear LLP

(57) ABSTRACT

A process for the production of fat-liquored, tanned leather or pelt is provided. The process comprises the steps of fat-liquoring and tanning, wherein an animal hide, skin or pelt is fat-liquored with a substituted acylaminopolyorganosiloxane (A) in the presence of a surfactant or surfactant mixture (B), which is an anionic or nonionic surfactant or mixture of anionic or/and non-ionic surfactants, before, during or/and after tanning, wherein the substituted acylaminopolyorganosiloxane (A) is a polyorganosiloxane containing substituted acylamino groups linked to silicon atoms of the polysiloxane skeleton via alkylene bridges or mono- or oligo-[alkylene-amino or alkylene-(substituted acyl)amino]-alkylene bridges. Also provided are tanned pelt or leather, certain substituted acylaminopolyorganosiloxanes (A') and related processes and compositions.

33 Claims, No Drawings

FAT-LIQUORING

RELATED APPLICATIONS

This application is the U.S. National Phase of International Application No. PCT/EP2013/000009, filed Jan. 3, 2013, designating the U.S. and published in English as WO 2013/110428 on Aug. 1, 2013 which claims the benefit of European Patent Application No. 12000556.6 filed Jan. 28, 2012.

FIELD

In the production of leather the various treatment steps for the treatment of the hide or skin up to tannage, lead to a loss of fat content and of the original soft handle of the substrate. In order to obtain a product of a certain desired fat content, suppleness, softness and handle there may be introduced suitable fats or oils, conventionally in emulsified form, into the substrate, and thus fat-liquoring is now a conventional essential treatment in order to provide lubricity of the fibers and fibrils of the leather texture to each other and thus to achieve some softness and handle properties of the substrate. There have been used natural fats and oils such as tallow, vegetable oils or marine animals oils and modified products thereof, or even substitutes of natural fats or oils. Due e.g. to environmental reasons, species protection reasons and availability reasons, many natural fats and oils and their derivatives have at least in part been replaced by synthetic fat-liquoring agents. Synthetic fat-liquoring agents, even polymeric substances which per se are not "fats" or "oils", have thus also found their use as fat liquors in more recent times. Thus e.g. in U.S. Pat. Nos. 5,279,613 and 5,575,939 and in WO-2009/080489 A1 there are described copolymers of certain olefins with dicarboxylic acid anhydrides, for use for fat-liquoring.

Another treatment of leather is water proofing, which in some cases may be combined with a fatting or fat-liquoring treatment. U.S. Pat. Nos. 5,702,490 and 6,110,230 and DE-19629986 disclose water proofing (hydrophobicizing) treatments of leather or pelts with certain polysiloxanes containing comb-like bonded carboxylic groups in the polymer structure, in particular with a metal salt aftertreatment; the metal salts being compounds of the kind as used conventionally for mineral tanning. In U.S. Pat. No. 6,379,751 there are described certain polysiloxanes containing carboxylic groups and carbonamido groups in the polymer structure, which are employed in combination with one or more further components (anionic copolymers, polyaspartic acid or derivatives, paraffins, isocyanate adducts) as water proofing agents for leather and pelts. DE-4214150 discloses certain polysiloxanes containing terminal sulphosuccinic acid monoester groups in the polymer structure, which are employed without any metal salt aftertreatment as water proofing agents for leather and pelts. US-2005/0043479 A1 discloses compositions comprising certain carboxyl-containing polysiloxanes and at least one aprotic substance liquid at RT or an organic solvent and with up to 2% of water which are applied by coating or spraying on a dry substrate having a fibrous structure (leather, fur skins or textile) and drumming to give a hydrophobicised or refatted substrate. Substrates treated in this way, i.e. with hydrophobicising polysiloxanes, are less suitable for further treatment from aqueous medium, such as e.g. dyeing. The hydrophobicising agents further tend to accumulate on and near the surface of the substrate so that their concentration on and close to the surface tend to be higher than in the inner region of the substrate texture. Any subsequent shaving would thus remove an essential portion of surface, substantially impairing the water proofing character of the treatment.

SUMMARY

It has now surprisingly been found that in the production of tanned and fat-liquored leather and pelts a fat-liquoring of animal hides, skins or pelts before, during or/and after tanning—in particular a full fat-liquoring or through-fatliquoring—of outstanding quality, can be achieved using the below defined polyorganosiloxanes (A) [substituted acylaminopolyorganosiloxanes (A)], in aqueous dispersion, in the presence of below defined surfactant (B), in particular even without any pre- or aftertreatment with a metal salt as otherwise used in mineral tanning. In this way there may be produced leathers and pelts of optimum properties, in particular suppleness, softness, penetration, tensile properties, fullness, firmness, grain structure, hydrophilicity and water vapour permeability—while fogging and formation of fatty spew or stain can be kept to a minimum—and the treated substrate may still be shaved without substantial loss of fat-liquoring effect.

The invention thus relates to the use of the defined polyorganosiloxanes (A), in the presence of defined nonionic or anionic surfactants (B) for fat-liquoring of animal hides, skins or pelts before, during or/and after tanning—where (A) may be in the form of a composition (F) which may also comprise (B)—, the fat-liquored leather or pelt and its use for further processing. The invention further relates to certain defined polyorganosiloxanes (A'), their compositions (F'), and their production.

DETAILED DESCRIPTION OF THE EMBODIMENTS

The invention thus firstly provides the use of a substituted acylaminopolyorganosiloxane (A) which is a polyorganosiloxane containing substituted acylamino groups linked to silicon atoms of the polysiloxane skeleton via alkylene bridges or mono- or oligo-[alkylene-amino or alkylene-(substituted acyl)amino]-alkylene bridges, wherein alkylene contains 2-4 carbon atoms and the substituted acylamino groups are at least in part of formula

and for the remaining part are selected from substituted acylamino groups of formulae

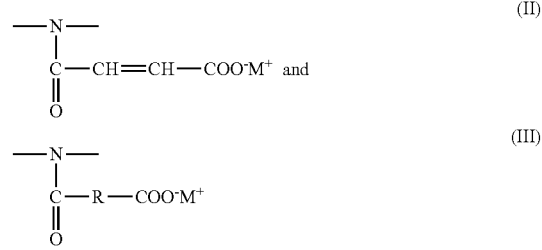

wherein

X1 signifies hydrogen or the group —SO$_3^-$M$^+$,

X2 signifies hydrogen or the group —SO$_3^-$M$^+$, with the proviso that one of X1 and X2 is —SO$_3^-$M$^+$ and the other is hydrogen, R signifies C$_{2-6}$-alkylene or cyclohexylene and M$^+$ signifies an alkali metal cation or an ammonium cation, in the presence of a surfactant or surfactant mixture (B), which is an anionic or non-ionic surfactant or mixture of anionic or/and non-ionic surfactants, in the production of tanned and fat-liquored leathers or pelts, as a fat-liquoring agent for fat-liquoring of animal hides, skins or pelts, before, during or/and after tanning.

The term "oligo" in the polysiloxanes (A) and also in the below mentioned polysiloxanes (S$_A$) and (S), preferably means 2, 3 or 4, more preferably 2.

The wording "for the remaining part" means that if any substituted acylamino groups other than those of formula (I) are present, they are selected from those of formulae (II) and (III).

Cation M$^+$ may be any alkali metal cation or ammonium cation as conventionally employed for salt formation in anionic compounds. Where M$^+$ signifies an ammonium cation, it is preferably a tertiary or quaternary ammonium cation, preferably of formula

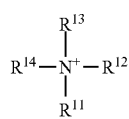

(IV)

wherein

R$^{11}$ is hydrogen or C$_{1-2}$-alkyl and each of R$^{12}$, R$^{13}$ and R$^{14}$ independently, is C$_{1-2}$-alkyl or C$_{2-3}$-hydroxyalkyl or R$^{12}$ and R$^{13}$ together with the neighbouring nitrogen form a 5- or 6-membered, saturated, N-containing heterocycle.

In R$^{11}$, R$^{12}$, R$^{13}$ and R$^{14}$, C$_{1-2}$-alkyl preferably is methyl.

In R$^{12}$, R$^{13}$ and R$^{14}$, as C$_{2-3}$-hydroxyalkyl there may be mentioned 2-hydroxypropyl-1 and preferably β-hydroxyethyl.

As alkali metal cations there may be mentioned in particular lithium, sodium or potassium, among which sodium is preferred. As ammonium cations there may be mentioned e.g. tetra(C$_{1-2}$-alkyl)-ammonium, tri(C$_{1-2}$-alkyl)-mono (C$_{2-3}$-alkanol)-ammonium, di(C$_{2-3}$-alkanol)-di(C$_{1-2}$-alkyl)-ammonium and mono(C$_{1-2}$-alkyl)-tri(C$_{2-3}$-alkanol)-ammonium. As heterocyclic cations there may be mentioned N-methyl-pyrrolidinium, N-methyl-piperidinium, N-ethyl-piperidinium, N-(2-hydroxyethyl)piperidinium, N-methyl-morpholinium, N-ethyl-morpholinium and N-(2-hydroxyethyl)morpholinium.

If the molecule contains any non-acylated amino groups the carboxylate or sulphonate anions may also form inner salts with them depending on the pH.

Preferably M$^+$ is an alkali metal cation, most preferably sodium.

C$_{2-6}$-alkylene in the significance of R may be linear or, if it contains 3-6 carbon atoms also branched. Cyclohexylene is preferably ortho. Preferably R is 1,2-propylene or most preferably ethylene.

The polyorganosiloxanes (A) may be produced by sulphiting methods conventional per se by introduction of sulpho groups into corresponding polyorganosiloxanes (S$_A$) containing substituted acylamino groups linked to silicon atoms of the polysiloxane skeleton via alkylene bridges or mono- or oligo-[alkylene-amino or alkylene-(substituted-acyl)amino]-alkylene bridges and which comprise as substituted acylamino groups monoamide groups of butenedioic acid and optionally of C$_{4-8}$-alkanedioic acid and/or cyclohexanedicarboxylic acid, by reaction of the olefinic double bond of butenedioic acid monoamide with a sulphiting reactant.

Herein and in the following text as "sulphiting" or "sulphitation" there is meant the reaction of an ethylenic double bond with the sulphiting reactant to give a sulphonate group bonded to the corresponding saturated ethylene group, in particular the reaction of the double bond of the butenedioic acid monoamide radical with the sulphiting reactant under basic conditions to form a sulphosuccinate monoamide group. As "sulphiting reactant" there is meant any such compound as suitable for the addition of sulphurous acid in a suitable derived salt form to the ethylenic double bond, in particular an alkali metal sulphite, bisulphite or metabisulphite or even, in the presence of alkali metal hydroxide, sulphur dioxide, among which bisulphite and especially metabisulphite, in particular sodium bisulphite or metabisulphite, are preferred.

The substituted acylaminopolyorganosiloxanes (A) as defined above may in particular be produced by a process in which a corresponding acylaminopolyorganosiloxane (S$_A$), which is a polyorganosiloxane containing substituted acylamino groups linked to silicon atoms of the polysiloxane skeleton via alkylene bridges or mono- or oligo-[alkylene-amino or alkylene-(substituted-acyl)amino]-alkylene bridges and wherein the substituted acylamino groups are of formula (II) or of formulae (II) and (III), and alkylene is C$_{2-4}$-alkylene, is reacted with a sulphiting reactant, in particular an alkali metal bisulphite or metabisulphite.

In the group of formula (I) obtainable in this way X2 preferably is hydrogen and X1 preferably is a sulphonate group —SO$_3^-$M$^+$.

The acylaminopolyorganosiloxanes (S$_A$) are known or may be produced by methods known per se or analogously to known methods, in particular by a process, wherein a corresponding aminopolyorganosiloxane (S) containing primary and/or secondary amino groups which are bonded to silicon atoms of the polysiloxane skeleton via alkylene bridges or mono- or oligo-(alkyleneamino)-alkylene bridges, wherein alkylene is C$_{2-4}$-alkylene, is reacted with (1) butenedioic acid anhydride or monochloride and optionally (2) the anhydride or monochloride of a C$_{4-8}$-alkanedioic acid or cyclohexylenedicarboxylic acid to give an acylaminopolyorganosiloxane (S$_A$) containing substituted amide groups of formula (II) and optionally (III).

For products (A) with a high degree of sulphitation, e.g. ≥70% of the carboxylate groups, it is preferred to use only (1). For the production of (A) with a lower degree of sulphitation, e.g. <70%, especially <50% of the carboxylate groups, a part of (1) may be replaced by (2) accordingly, if desired.

Butenedioic acid anhydride or monochloride is in particular maleic acid anhydride or monochloride or/and fumaric acid monochloride.

As starting aminopolyorganosiloxanes (S) are suitable any desired amino-substituted polyorganosiloxanes which contain corresponding Si-bonded aminoalkyl groups or amino-mono- or -oligo-(alkyleneamino)-alkyl groups. Suitable in general are any desired corresponding aminopolyorganosiloxanes having a polycationic or respectively polybasic character, essentially those built up from recurring dimethylsiloxy units and the defined aminosiloxy units, i.e. siloxy units containing Si-bonded aminoalkyl groups or amino-mono- or -oligo-(alkyleneamino)-alkyl groups. They may have a linear constitution or also a branched and/or crosslinked constitution (for example mono- or poly-branched or -crosslinked). The end groups may contain a reactive substituent, in particular, for example, hydroxy or alkoxy, or may optionally also be blocked, for example with trimethylsiloxy.

Preferably they have a substantially comb-like constitution, in which the siloxy units form a linear chain with pendant Si-bonded aminoalkyl groups or amino-mono- or -oligo-(alkyleneamino)-alkyl groups randomly distributed along the chain.

The aminopolyorganosiloxanes (S) are preferably built up from units of the following formulae:

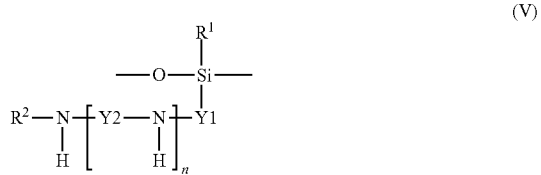

(V)

wherein
$R^1$ signifies methyl or methoxy,
$R^2$ signifies hydrogen or $C_{1-4}$-alkyl,
Y1 signifies 1,2- or 1,3-propylene or 2-methyl-1,3-propylene,
Y2 signifies ethylene or propylene, and
n signifies 0, 1 or 2,
and

(VI)

The end groups preferably are of the formula:

(VII)

wherein
$R^3$ signifies methyl, methoxy or hydroxy.

Expediently the dimethylsiloxy units are in numerical excess over the siloxy units containing the amino groups. Preferably there are at least 4, more preferably 4 to 70, dimethylsiloxy groups for every siloxy unit containing amino.

Aminopolyorganosiloxanes (S) preferably are aminopolyorganosiloxanes of the average statistic formula

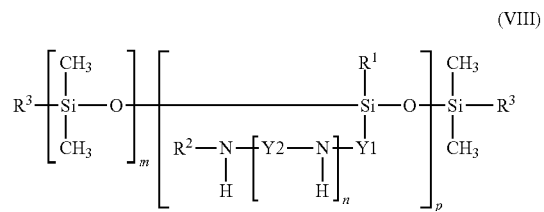

(VIII)

wherein
m is 4 to 400,
p is 1 to 60,
the ratio m/p is in the range of 4-70
and the symbols
$R^1$, $R^2$, $R^3$, Y1, Y2 and n have the significances indicated above.
Preferably in (S)
$R^1$ signifies methyl,
$R^2$ signifies hydrogen,
$R^3$ signifies methyl or methoxy,
Y1 signifies 1,3-propylene,
Y2 signifies ethylene,
$M^+$ signifies an alkali metal cation,
n signifies 1,
m signifies 8-200 and
m/p is in the range of 8-20.

The aminopolyorganosiloxanes (S) may be characterized by typical parameters which are customary per se, for example by their average molecular weight and the content of amine nitrogen, and also by their viscosity. The average molecular weight and the content of amine nitrogen of the aminopolyorganosiloxanes (S) can vary in broad ranges, aminopolyorganosiloxanes (S) with a low amine value being preferred, particularly those as stated above with an amine value in the range of 1 to 3.5 milliequivalents amino group per 1 g of (S), more preferably 1.2 to 2.5 milliequivalents amino group per 1 g of (S)—one equivalent amino group being one equivalent of acylatable amino group.

The aminopolyorganosiloxanes (S) advantageously have a viscosity in the range 20-30,000, principally 50-10,000, preferably 80-1000 cP (Brookfield rotational viscometer RV, spindle No. 5, 20° C.). The average molecular weight $\overline{M}_W$ of (S) is e.g. in the range of 500 to 300,000, advantageously in the range from 600 to 150,000, preferably from 700 to 100,000, more preferably from 800 to 40,000. Molecular weights may be determined by conventional methods, e.g. by gel permeation chromatography against polydimethylsiloxane standards.

The ratio m/p of the number of dimethylsiloxy units to the number of amino-group-containing siloxy units present in the molecule [i.e. aminoalkylsiloxy units and/or amino-mono- or -oligo-(alkyleneamino)-alkylsiloxy units] is preferably in the range from 6/1 to 40/1, more preferably 8/1 to 20/1.

The aminopolyorganosiloxanes (S) may be produced in a manner known per se or analogously to known methods, for example by aminoalkylation of polysiloxanes containing reactive Si-bonded hydrogen atoms, or principally by copolymerization of amino-containing silanes with corresponding non-ionogenic silanes or polysiloxanes or cyclic siloxanes.

The aminoalkylation can take place under conditions known per se, using conventional aminoalkylating agents or respectively hydrosilylating agents, for example with allylamine.

For the copolymerization, the amino-containing silanes are preferably copolymerized with α,ω-dihydroxypolydimethylsiloxane, advantageously having an average molecular weight $\overline{M}_W$ in the range from 300 to 10,000, preferably from 400 to 7000, or/and with cyclic siloxanes, for example hexamethylcyclotrisiloxane, octamethylcyclotetrasiloxane, decamethylcyclopentasiloxane, dodecamethylcyclohexasiloxane and technical-grade mixtures of two or more thereof. Suitable amino-containing silanes include principally trimethoxysilanes or dimethoxy- or -ethoxymethylsilanes which are aminoalkyl-substituted or amino-mono- or -oligo-(alkyleneamino)-alkyl-substituted on Si, in which the Si-bonded aminoalkyl group or amino-mono- or -oligo-(alkyleneamino)-alkyl group advantageously conforms to the formula

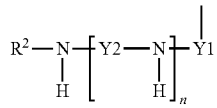

(IX)

preferably $$H_2N\text{—}(Y2\text{-}NH)_n\text{—}Y1\text{-}$$ (X)

More preferably this group is 3-[N-(β-aminoethyl)-amino]-propyl.

The copolymerization can be carried out in a manner known per se, principally by reaction of the reactants at moderate or elevated temperature, optionally under reduced pressure, in particular at temperatures in the range 15-180° C., optionally in the presence of a catalyst and, if desired, with use of end-blocking groups, for example with hexamethyldisiloxane. As catalysts, use can be made of acids (in particular formic acid, acetic acid, sulphuric acid, acidic ion exchangers or trifluoromethanesulphonic acid) or of alkali metal or ammonium compounds, for example alkali metal or ammonium silanolates (for example potassium silanolate or tetramethylammonium silanolate) or alkali metal hydroxides or ammonium hydroxides, which form the corresponding silanolates in situ with the respective silanes, or else alkali metal hydroxides, carbonates or bicarbonates (for example potassium hydroxide, sodium hydroxide or sodium bicarbonate) or further benzyltrimethylammonium hydroxide or tetrabutylammonium hydroxide. If desired, the polymerisation can be carried on for equilibration, e.g. for 30 minutes to 8 hours, preferably from 1 to 6 hours. If desired it may be carried out in the presence of an inert solvent, e.g. methyl-ethyl-ketone or tetrahydrofuran, which can then be removed, for example by distillation, under polymerisation conditions or subsequently, or in the presence of a diluent, e.g. mineral oil, preferably mineral oil with a boiling range below 300° C. and above 200° C., which can then be removed, for example by distillation under reduced pressure.

[The above formula (VIII), and also the below formulae (XVII), (XVIII), (XXVI) and (XXVII), merely serve for illustration of the monomer units occurring and their number, but not their distribution or position in the polymer molecule.]

Depending on the production conditions selected, the amino-group-containing units in the molecule—for example in the molecule of the formula (VIII)—may be randomly distributed or may be terminal or may be grouped as in block polymers or may also accumulate towards the extremities of the linear chains.

If desired, substituted acylaminopolyorganosiloxanes (A) may be used in admixture with polydimethylsiloxane, e.g. having an average molecular weight $\overline{M}_W$ in the range from 200 to 2000, preferably from 300 to 1500, which may be added after completion of the synthesis or the polymerisation conditions and reactant ratios in the production of (S) may be chosen in such a way that some unsubstituted polydimethylsiloxane is present, e.g. up to 50% by weight of (S), in particular 5 to 50% by weight of (S). If (A) is in admixture with unsubstituted polydimethylsiloxane, the latter is preferably present in a ratio of 8 to 40% by weight of (A).

For the production of the modified polysiloxanes $(S_A)$ and of the modified polysiloxanes (A), preference is given to those aminopolyorganosiloxanes (S) which possesses a preponderantly linear constitution of the polysiloxane skeleton, in which the units of the formula (V)—where there is more than one unit per molecule—are randomly distributed throughout the molecule in a comb-like manner.

The aminopolyorganosiloxanes (S) may be acylated with the mentioned acylating agents (1) and optionally (2) to give the corresponding acylaminopolyorganosiloxanes $(S_A)$ containing substituted amide groups of formula (II) and optionally (III).

The acylation can take place under conditions which are conventional per se, for example, by simple mixing of the reaction components, optionally in the presence of an organic solvent or diluent, e.g. methyl-ethyl-ketone or tetrahydrofuran, or mineral oil with boiling range <300° C. and >200° C., under mild temperature conditions, for example at temperatures in the range from 10 to 90° C., preferably 20-80° C. The corresponding protonated form of any basic amino group still present in the molecule may simultaneously be formed.

The reaction with acylating agents (1) and (2) may be carried out in any desired sequence or even simultaneously. If acylating agent (2) is used, it is preferably reacted first and acylating agent (1) is preferably reacted after acylating agent (2).

The molar ratio of the acylating agents (1) and (2) to the amino groups present in (S) is preferably sufficient for acylation of at least 70%, preferably 80-98% more preferably 88-97% of the available amino groups.

The degree of acylation may be determined by titration of the carboxylate groups present and indicated as "anionicity value" or "carboxylate number", in milliequivalents carboxylate anion per 1 g of $(S_A)$.

The anionicity value (acid number relating to the carboxylate groups or "carboxylate number") of the acylaminopolyorganosiloxane $(S_A)$ preferably is in the range of 0.8 to 2.6 milliequivalents carboxylate anion per 1 g of $(S_A)$, more preferably 1 to 2 milliequivalents carboxylate anion per 1 g of $(S_A)$.

Acylating agent (1) is preferably employed in such proportion that at least 50% of the acylatable amino groups more preferably 60-98%, still more preferably 75-97% thereof are acylated with (1). Acylating agent (2) is preferably employed in a minor proportion, e.g. up to 50% of (1), or even is not employed at all, but the only acylating agent is (1).

Among the anhydrides and the monochlorides the anhydrides are preferred as acylating agents, the most preferred acylating agent being maleic anhydride.

The produced acylaminopolyorganosiloxane $(S_A)$ may be isolated from the reaction mixture or, if desired, may be directly further reacted with the sulphiting reactant to give (A).

The produced acylaminopolyorganosiloxane ($S_A$) contains acylated derivatives of the amino groups of the aminopolyorganosiloxane (S) in particular of those of formula (IX). These acylated derivatives of the groups of formula (IX) preferably correspond to formula

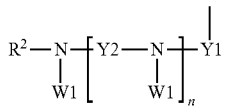 (XI)

wherein
W1 independently signifies hydrogen or a group selected from the groups of formula

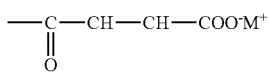 (XII)

and, if an acylating agent (2) has been used, also of formula

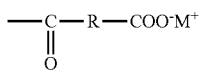 (XIII)

at least one symbol W1 signifying a radical of formula (XII).

Preferred acylaminopolyorganosiloxanes ($S_A$) produced as described above thus contain units of formula

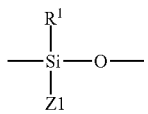 (XIV)

wherein
$R^1$ signifies methyl or methoxy, and
Z1 is a radical of formula (XI), together with recurring dimethylsiloxy units.

Depending on the proportion of acylating agent (1) and—if used—(2) the molecule may also contain units of formula

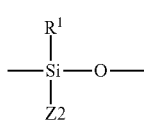 (XV)

in which Z2 is a radical of formula

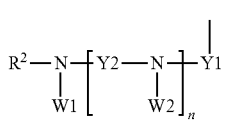 (XVI)

wherein W2 independently signifies hydrogen or a radical of formula (XIII).

Corresponding preferred acylaminopolyorganosiloxanes ($S_A$) may thus be represented by the average statistic formula

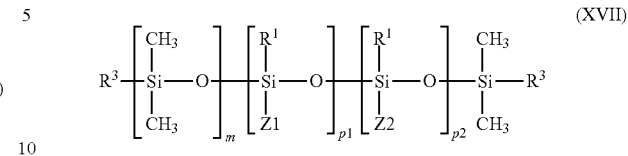 (XVII)

wherein
the symbols $R^1$, $R^3$, Z1, Z2 and m have the significances indicated above,
p1 is 1 to 60,
p2 is 0 to 30,
p1+p2=p,
p1 is ≥0.5 p and
p is 1 to 60 as indicated above.

If, according to a preferred feature, acylating agent (1) is used in sufficiently high proportion, especially as described above, in particular so that 75-98%, more preferably 85 to 98% of the acylatable amino groups are acylated with acylating agent (1), the corresponding more preferred acylaminopolysiloxanes ($S_A$) may be represented by the average statistic formula

 (XVIII)

wherein
the symbols $R^1$, $R^2$, $R^3$, Y1, Y2, W1, m, n and p have the significances indicated above.

In the acylated product ($S_A$) preferably
$R^1$ signifies methyl,
$R^2$ signifies hydrogen,
$R^3$ signifies methyl or methoxy,
Y1 signifies 1,3-propylene,
Y2 signifies ethylene,
$M^+$ signifies an alkali metal cation,
n signifies 1,
m signifies 8-200 and
m/p is in the range of 8-20.

For the production of the substituted acylaminopolyorganosiloxanes (A) the sulphiting reaction of the acylaminopolyorganosiloxanes ($S_A$) with the sulphiting reactant for the introduction of a sulpho group may be carried out under conditions conventional per se, preferably in aqueous or aqueous/organic medium. The sulphiting reactant may be any such compound as suitable for the addition of sulphurous acid in a suitable derived salt form to the ethylenic double bond, in particular an alkali metal sulphite, bisulphite or metabisulphite or even (in the presence of alkali metal hydroxide) sulphur dioxide, among which bisulphite and especially metabisulphite are preferred. Alkali metal preferably is potassium or most preferably sodium. The reaction takes place in aqueous or aqueous/organic medium, preferably at a pH in the range of 4-9, more preferably 4.5-7.5. For salt formation, and/or—where required—for pH adjustment, a conventional suitable base may be used, most preferably sodium hydroxide. If desired an organic solvent or diluent that does not interfere with the reaction may be present, e.g. methyl-ethyl-ketone or tetrahydrofuran or mineral oil with boiling range <300° C. and >200° C. (e.g. in order to improve the stirrability of the reaction mixture), especially if it was present in ($S_A$) during acylation of (S) to ($S_A$). The sulphiting reaction may be carried out under mild temperature conditions, e.g. at temperatures in the range of 10 to 70° C., preferably 20 to 45° C., and may be completed by slightly heating the reaction mixture, suitably to temperatures in the range of 50 to 80° C., as may be required in order to eliminate (under reduced pressure, if required) any undesired components such as by-products, solvents, diluents or/and catalysts, from the product. The above mineral oil may, if desired, be evaporated e.g. at about 150° C. under reduced pressure.

The substituted acylaminopolyorganosiloxanes (A) are, in particular, preferably polyorganosiloxanes containing recurring dimethylsiloxy units and units of formula

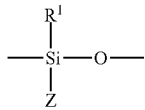
(XIX)

wherein
$R^1$ signifies methyl or methoxy,
Z is a radical of formula

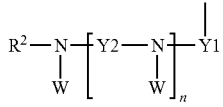
(XX)

$R^2$ signifies hydrogen or $C_{1-4}$-alkyl,
Y1 signifies 1,2- or 1,3-propylene or 2-methyl-1,3-propylene,
Y2 signifies ethylene or propylene,
n signifies 0, 1 or 2 and
W independently signifies hydrogen or a group selected from the groups of formulae (XII), (XIII) and

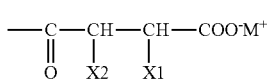
(XXI)

with the proviso that at least one of the n+1 symbols W signifies a group of formula (XXI).

In the radical Z the substituent W is preferably only a radical of formula (XXI), or also—where n is 1 or 2—at least one of the substituents W is a radical of formula (XXI) and at least one symbol W signifies hydrogen or a radical of formula (XII) or (XIII).

More particularly Z preferably is selected from Z3 which is a radical of formula

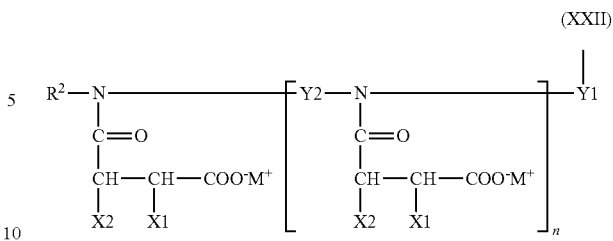
(XXII)

and Z4 which is a radical of formula

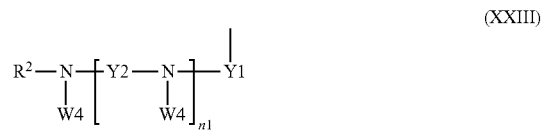
(XXIII)

wherein
n1 signifies 1 or 2 and
W4 independently signifies hydrogen or a group selected from the groups of formulae (XII) or (XIII) or (XXI) at least one of the n1+1 symbols W4 signifying a group of formula (XXI) and at least one signifying hydrogen or a group of formula (XII) or (XIII).

The polymer may also contain constituent units which in the substituted acylamino groups do not contain any sulpho group, which may in particular depend on the chosen molar ratios of the reactants and/or on the chosen reaction conditions. Substituted acylaminopolysiloxane (A) may thus further contain constituent units of formula

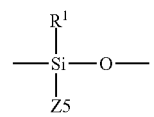
(XXIV)

wherein
Z5 is a radical of formula

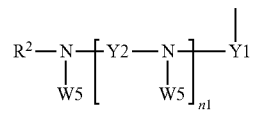
(XXV)

and W5 independently signifies hydrogen or a group selected from the groups of formulae (XII) or (XIII).

Expediently the dimethylsiloxy units are in numerical excess over the siloxy units containing the acylamino groups. Preferably there are at least 4, more preferably 4 to 70, dimethylsiloxy groups for every siloxy unit containing acylamino and/or amino.

Of the acylamino groups present in substituted acylaminopolyorganosiloxanes (A) preferably at least 20% are of formula (I). More preferably 20 to 98%, most preferably 25 to 95%, of the number of substituted acylamino groups present in (A) are of formula (I).

Preferred substituted acylaminopolyorganosiloxanes (A) may be represented by the general statistic average formula (XXVI)

$$R^3-\underset{\underset{CH_3}{|}}{\overset{\overset{CH_3}{|}}{Si}}-O{\left[\underset{\underset{Z}{|}}{\overset{\overset{R^1}{|}}{Si}}-O\right]}_m {\left[\underset{\underset{Z5}{|}}{\overset{\overset{R^1}{|}}{Si}}-O\right]}_{p3}{\left[\underset{\underset{Z5}{|}}{\overset{\overset{R^1}{|}}{Si}}-O\right]}_{p4}\underset{\underset{CH_3}{|}}{\overset{\overset{CH_3}{|}}{Si}}-R^3$$

wherein
$R^1$ signifies methyl or methoxy,
$R^3$ signifies methyl, methoxy or hydroxy,
m signifies 4 to 400,
Z is a radical of formula (XX),
Z5 is a radical of formula (XXV),
p3 signifies 1 to 15,
p4 signifies 0 to 4 p3,
p3+p4=p and
the ratio of m/(p3+p4) is in the range of 4-70,
or, in more detail, may be represented by the general statistic average formula (XXVII)

$$R_3-\underset{\underset{CH_3}{|}}{\overset{\overset{CH_3}{|}}{Si}}-O{\left[\underset{\underset{Z3}{|}}{\overset{\overset{R_1}{|}}{Si}}-O\right]}_m{\left[\underset{\underset{Z4}{|}}{\overset{\overset{R_1}{|}}{Si}}-O\right]}_{p5}{\left[\underset{\underset{Z5}{|}}{\overset{\overset{R_1}{|}}{Si}}-O\right]}_{p6}{\left[\underset{\underset{Z5}{|}}{\overset{\overset{R_1}{|}}{Si}}-O\right]}_{p4}\underset{\underset{CH_3}{|}}{\overset{\overset{CH_3}{|}}{Si}}-R_3$$

wherein
p5 signifies 0 to 15,
p6 signifies 0 to 15,
p5+p6=p3 and
p4+p5+p6=p.

Among the sulphited acylaminopolyorganosiloxanes (A) are preferred those in which
$R^1$ signifies methyl,
$R^2$ signifies hydrogen,
$R^3$ signifies methyl or methoxy,
Y1 signifies 1,3-propylene,
Y2 signifies ethylene,
$M^+$ signifies an alkali metal cation,
n signifies 1,
m signifies 8-200 and
m/p is in the range of 8-20.

The degree of sulphitation, indicating the sulpho group content in the substituted acylaminopolysiloxane (A), may be expressed by the sulphonate number, which may be determined by calculating the amount of sulphite that has reacted with $(S_A)$ and determining titrimetrically any residual sulphite still present in the reaction mixture after completion of the sulphitation reaction (the difference of the amount of sulphite given into the reaction mixture minus the residual amount of non-reacted sulphite in the mixture indicates the amount of sulphite that has reacted with the double bond to give the sulphonate group).

Preferably the sulphonate number of the substituted acylaminopolysiloxane (A) is in the range of 0.4 to 1.6 milliequivalents sulpho groups per 1 g of substituted acylaminopolysiloxane (A).

The substituted acylaminopolysiloxanes (A), in particular produced as described above, have a distinct, more or less pronounced hydrophilicity and can be diluted with water to give aqueous compositions (F). These contain preferably 2 to 60% by weight, more preferably 4 to 40% by weight, of (A) referred to (F).

For use as a fat-liquoring agent the substituted acylaminopolysiloxane (A) is combined with one or more non-ionic or/and anionic surfactants (B). Preferably surfactant (B) is also included in the aqueous composition (F).

Suitable surfactants (B) are generally any desired non-ionic or anionic surfactants, preferably those which emulsify polysiloxanes, principally OWN (oil-in-water) emulsifiers (the oil "O" in this case stands for silicone oil), more preferably hydrophilic O/W emulsifiers. If desired W/O-emulsifiers may be used in addition to O/W-emulsifiers. Surfactants (B) are advantageously surfactants or surfactant mixtures selected from:

(B1) $C_{9-24}$-aliphatic alcohol oligo- or poly($C_{2-3}$-alkylene) glycolethers, $C_{9-24}$-aliphatic carboxylic acids oligo- or poly($C_{2-3}$-alkylene)glycolesters, (B2) mono- and/or diesters of maleic, fumaric or succinic acid with $C_{9-24}$-aliphatic alcohol oligo- or poly($C_{2-3}$-alkylene)glycolethers or with $C_{9-24}$-aliphatic carboxylic acids oligo- or poly($C_{2-3}$-alkylene)glycolesters, (B3) sulphonated (sulphited) mono- and/or diesters of maleic or fumaric acid with $C_{9-24}$-aliphatic alcohol oligo- or poly($C_{2-3}$-alkylene)glycolethers or of $C_{9-24}$-aliphatic carboxylic acids oligo- or poly($C_{2-3}$-alkylene)glycolesters, (B4) $C_{9-24}$-aliphatic alcohol oligo- or poly($C_{2-3}$-alkylene) glycolether phosphates or $C_{9-24}$-aliphatic carboxylic acid oligo- or poly($C_{2-3}$-alkylene)glycolester phosphates, (B5) $C_{9-24}$-aliphatic sulphonates, $C_{4-18}$-alkylbenzene sulphonates, (B6) $C_{9-24}$-fatty acid sarcosides, (B7) glycerol or sorbitan mono- and/or diesters of $C_{9-24}$-aliphatic carboxylic acids, (B8) maleic, fumaric or succinic acid mono-$C_{9-24}$-aliphatic amides, (B9) sulphonated (sulphited) derivatives of maleic or fumaric acid mono-$C_{9-24}$-aliphatic amides, and mixtures of two or more thereof.

The $C_{9-24}$-aliphatic carboxylic acids are preferably the radicals of $C_{12-24}$-fatty acids, which may be saturated or unsaturated, preferably monoethylenically unsaturated, (e.g. lauric, myristic, palmitic, stearic, arachidic, behenic, palmitoleic, oleic or erucic acid). The $C_{9-24}$-aliphatic alcohols are preferably $C_{12-24}$-fatty alcohols which may be saturated or unsaturated preferably monoethylenically unsaturated, (e.g. lauryl, myristyl, cetyl, stearyl or oleyl alcohol) or $C_{9-13}$-oxoalcohols. The $C_{9-24}$-aliphatic radicals in (B5), (B8) and (B9) are preferably $C_{12-24}$-fatty radicals (alkyl or alkenyl) which may be saturated or unsaturated, the unsaturated ones being preferably monoethylenically unsaturated, (e.g. lauryl, myristyl, cetyl, stearyl or oleyl).

In surfactants (B1), (B2), (B3) and (B4) oligo signifies 2-10 units. The $C_{2-3}$-alkylene groups in the oligo- or poly ($C_{2-3}$-alkylene)glycol chains are preferably either only ethylene or ethylene and propylene. In the oligo- or poly ($C_{2-3}$-alkylene)glycol chains the number of ethylenoxy groups is preferably ≥40% of the total ethylenoxy and propylenoxy groups. The average number of $C_{2-3}$-alkylenoxy units in the oligo- or poly($C_{2-3}$-alkylene)glycol chains is preferably 2-40, more preferably 2-20, most preferably 3-12. Most preferably $C_{2-3}$-alkylene is only ethylene.

Among the above surfactants (B1)-(B9) the sulphonates (B3), (B5) and (B9) and phosphates (B4), particularly the sulphonates (B3), (B5) and (B9), are preferred, especially the esters (B3). Among the surfactants (B3) are particularly preferred the sulphonated (sulphited) diesters of maleic acid with $C_{9-24}$-aliphatic carboxylic acids oligo or poly($C_{2-3}$-alkylene)glycolesters.

Among the surfactants (B1), (B2), (B6), (B7) and (B8) the esters (B2) and sarcosides (B6) are preferred, in (B2) especially diesters of maleic acid with $C_{9-24}$-aliphatic carboxylic acids oligo or poly($C_{2-3}$-alkylene)glycolesters, in (B6) especially N-lauroyl-, N-stearoyl- and N-oleoyl-sarcosine.

According to a preferred feature of the invention one or more of the surfactants (B3), (B4), (B5) and (B9), preferably (B3) or (B5), are used in admixture with one or more of the surfactants (B1), (B2), (B6), (B7) and (B8), preferably (B2), (B6) or (B7). The quantitative ratio of the former [(B3), (B4) or/and (B5)] to the latter [(B1), (B2), (B6) or/and (B7)] being e.g. in the range of 2/8 to 9/1, preferably 5/5 to 8/2. Particularly preferred surfactants combinations are the combination of (B3) with (B2) and/or (B6), the combination of (B8) with (B9), and the combination of (B4) with (B6).

The emulsifiers (B) can be employed in any desired suitable quantitative ratios to the modified polysiloxanes (A), as are suitable or preferred for the respective desired purpose. Suitable weight ratios (B)/(A) are, for example, in the range of from 1 to 150, preferably 1.5 to 80 parts by weight of (B) for every 100 parts by weight of (A). The concentration of (B) in (F) may vary in a broad scope, preferably in the range from 1/100 to 50/100, preferably 1/100 to 40/100, more preferably from 2/100 to 30/100 by weight of (B) referred to (F).

According to a particular procedure surfactant (B) may be present during the reaction of $(S_A)$ with the sulphiting reactant and even during the acylating reaction of (S) to $(S_A)$. Surfactants (B2) which are mono- and/or diesters of maleic or fumaric acid and/or their sulphited derivatives (B3), or surfactants (B8) which are monoamides of maleic or fumaric acid and/or their sulphited derivatives (B9), are particularly preferred for this purpose.

According to a particularly preferred procedure the sulphitation of maleic or/and fumaric acid mono- and/or diesters (B2) to corresponding sulphosuccinates (B3) or of maleic or/and fumaric acid monoamides (B8) to corresponding sulphosuccinamides (B9) may be carried out in the same reaction sequence in which $(S_A)$ is sulphited to (A), in particular before or during the reaction of $(S_A)$ with the sulphiting reactant.

The content in sulpho groups of the reaction product may be determined by conventional methods, e.g. by Epton-titration with Hyamine® 1622, which is Benzethonium chloride, i.e. Benzyl-dimethyl-(4-{2-[4-(1,1,3,3-tetramethylbutyl)-phenoxy]-ethoxy}-ethyl)-ammonium chloride, e.g. according to standard method ASTM-D 1681-05, and may be expressed in % $-SO_3^-$ referred to the reaction product mass.

If desired, formulation additives (C) can be added in (F). There may be employed formulation additives (C) as are suitable for maintaining the physical form of the formulation and/or for achieving a suitable quality of the liquid formulation, for example with a view to the intended use and/or the type of the envisaged packaging and storage and/or to the envisaged transport means for supply.

Formulation additives (C) which come into consideration are principally agents for influencing the liquid form of the aqueous composition, especially:
(C1) defoamers,
(C2) hydrotropes,
(C3) rheology assistants (=viscosity modifiers),
and/or
(C4) acids and/or bases and/or buffers for pH adjustment.

Defoamers (C1) may be e.g. silicones or preferably paraffins or paraffin oil. They may be employed in very low concentrations, for example in the range from 0.05 to 5% by weight, preferably from 0.1 to 2% by weight, based on (A).

Auxiliaries (C2) and (C3) which come into consideration are essentially those which are suitable for influencing the colloidal form and/or the flow behaviour of the aqueous compositions (F).

Hydrotropes (C2) which can be mentioned are compounds which are conventional per se, for example urea, $C_{2-6}$-alkanediols (for example hexylene glycol, butanediol, propylene glycol) or di($C_{2-4}$-alkylene) glycols (for example dipropylene glycol), their monoethers of low-molecular-weight aliphatic alcohols, for example of $C_{1-4}$-alkanols (for example butyl glycol, i.e. ethylene glycol monobutyl ether) and oligoethylene glycols (for example having an average molecular weight in the range from 200 to 400). They can be employed in concentrations conventional per se, for example in the range from 1 to 50% by weight, principally from 2 to 25% by weight, based on (A).

The term rheology assistants (C3) here is generally taken to mean auxiliaries which are suitable for influencing, in particular reducing or setting to certain values, the viscosity of the aqueous composition, above all water-soluble salts (having a water solubility of, for example, at least 3% by weight at room temperature), advantageously alkali metal salts of organic or inorganic acids, for example sodium acetate, chloride or cumenesulphonate. They may be employed in very low concentrations, for example in the range from 0.005 to 1% by weight, principally from 0.01 to 0.5% by weight, preferably from 0.025 to 0.25% by weight, based on (A).

As acids, bases and buffers (C4) there may be employed known substances as suitable for setting or maintaining a pH e.g. in the range of 4-8, e.g. as acids acetic or formic acid, as bases alkali metal hydroxides or carbonates, hydroxides of ammonium cations of formula (IV) or tertiary amines, as buffers, e.g. sodium or potassium phthalate, oxalate or citrate, sodium or/and potassium mono- and/or di-hydrogen-phosphate or a mixture of phosphoric acid and sodium or/and potassium di-hydrogenphosphate, preferably a combination of $KH_2PO_4$ or $NaH_2PO_4$ and $Na_2HPO_4$ or $K_2HPO_4$.

The concentration of components (C), if any, is preferably low; preferably the concentration of the total of (C) is in the range of 0 to 10% by weight of (C) referred to (F).

If desired, composition (F) may comprise
(D) agents for protection against the damaging action of micro-organisms.

Agents (D) for protection against the damaging action of micro-organisms which come into consideration are principally agents for inhibiting the growth of harmful bacteria or other microbes, or also microbicides, above all fungicides. They can be employed in very small amounts. Suitable products are generally those as are commercially available, and they can also be employed in the corresponding recommended concentrations, for example in concentrations in the range of 0 to 2% by weight of (D) referred to (F), preferably in the range from 0.001 to 0.5% by weight, more preferably from 0.04 to 0.1% by weight of active substance, based on the aqueous composition (F).

The dry substance content of (F) preferably is in the range of 4 to 70% by weight, more preferably in the range of 10-60% by weight.

Aqueous composition (F) are preferred containing
(a) =2 to 60% by weight of (A) referred to (F),
(b) =1 to 40%, preferably 2 to 30% by weight of (B) referred to (F),
(c) =0 to 10% by weight of (C) referred to (F) and
(d) =0 to 2% by weight of (D) referred to (F),
and the dry substance content of which is in the range of 4 to 70% by weight.

As mentioned above, substituted acylaminopolyorganosiloxanes (A) are employed in the presence of surfactants (B) for fat-liquoring of animal hides, skins or pelts before, during and/or after tanning. Expediently substituted acylaminopolyorganosiloxanes (A) and surfactants (B) are employed in the form of the above described aqueous compositions (F) comprising (A) and (B), and which may also comprise further components (C) and/or (D).

According to a particular feature, the invention further provides certain substituted acylaminopolyorganosiloxanes (A), namely substituted acylaminopolysiloxanes (A')
in particular for use in the fat liquoring process of the invention—which are polyorganosiloxanes containing substituted acylamino groups linked to silicon atoms of the polysiloxane skeleton via mono- or oligo-[alkyleneamino or alkylene-(substituted acyl)amino]-alkylene bridges, wherein alkylene contains 2-4 carbon atoms and the substituted acylamino groups are at least in part of formula (I) as defined above, and for the remaining part are selected from substituted acylamino groups of formula (II) and (III) as defined above.

Preferred substituted acylaminopolysiloxanes (A'), are those containing recurring dimethylsiloxy units and units of formula (XIX) defined above, in which n signifies 1 or 2, preferably 1, more particularly those in which in the above formulae (XX) and (XXII) n signifies 1 or 2, preferably 1, and which may further contain units of formula (XXIV) defined above in which n signifies 1 or 2, preferably 1.

Preferred substituted acylaminopolysiloxanes (A') may be represented by general average statistic formula (XXVI) defined above with the proviso that in Z and in Z5 n signifies 1 or 2, or more particularly by general average statistic formula (XXVII) defined defined above, with the proviso that n signifies 1 or 2.

The particular further description and preferences stated above for substituted acylaminopolysiloxanes (A) apply also to substituted acylaminopolysiloxanes (A).

Substituted acylaminopolysiloxanes (A') may be synthesized by the processes indicated above for substituted acylaminopolysiloxanes (A), in particular by a process wherein an acylaminopolysiloxane ($S_A$') which is a polyorganosiloxane containing substituted acylamino groups linked to silicon atoms of the polysiloxane skeleton via mono- or oligo-[alkylene-amino or alkylene-(substituted acyl)amino]-alkylene bridges and wherein the substituted acylamino groups are of formula (II) or of formulae (II) and (III) defined above, is reacted with a sulphiting reactant.

Analogously as described above for ($S_A$) the acylated groups in ($S_A$') preferably correspond to formula (XI) defined above, with the proviso that n signifies 1 or 2. Thus also in formula (XVI), if present in ($S_A$'), n is 1 or 2.

The particular further description and preferences stated above for substituted acylaminopolysiloxanes ($S_A$) apply also to substituted acylaminopolysiloxanes ($S_A$').

Substituted acylaminopolysiloxanes ($S_A$') may be synthesized by the processes as indicated above for substituted acylaminopolysiloxanes ($S_A$), in particular by a process wherein an aminopolysiloxane (S) containing primary and/or secondary amino groups which are bonded to silicon atoms of the polysiloxane skeleton via mono- or oligo-(alkyleneamino)-alkylene bridges, is reacted with
(1) butenedioic acid anhydride or monochloride and optionally
(2) the anhydride or monochloride of a $C_{4-8}$-alkanedioic acid or cyclohexylenedicarboxylic acid
to give an acylaminopolyorganosiloxane ($S_A$') containing substituted amide groups of formula (II) and optionally (III).

A process for the production of acylaminopolysiloxanes (A') is in particular a process in which an aminopolysiloxane (S') is reacted with above reactants (1) and optionally (2) to give ($S_A$'), and ($S_A$') is reacted with a sulphiting reactant.

Where (S') comprises formulae (V) or (X) n is 1 or 2, more preferably 1. Analogously as described above for (S), (S') preferably corresponds to formula (VIII) defined above, with the proviso that n signifies 1 or 2, more preferably 1.

The particular further description and preferences stated above for aminopolysiloxanes (S) apply also to aminopolysiloxanes (S').

As described above for (A) also the process for the production of (A') may be carried out in the presence of (B) an anionic or non-ionic surfactant or mixture of anionic or/and non-ionic surfactants.

For use as a fat liquoring agent, (A') is advantageously employed in the form of an aqueous composition (F') comprising a substituted acylaminopolysiloxane (A') and preferably also a surfactant or surfactant mixture (B). The invention thus further provides a composition (F')—in particular for use as fat liquoring agent—comprising a substituted acylaminopolysiloxane (A') and preferably also a surfactant or surfactant mixture (B) as defined above.

Analogously as described above for (F) compositions (F') may advantageously further comprise component (C) defined above and/or component (D) defined above.

There may be produced—as described above—compositions (F) comprising a substituted acylaminopolyorganosiloxane (A) and a surfactant or surfactant mixture (B) and which may also comprise additives (C) and/or (D) defined above, of satisfactory stability as suitable for storage and shipment and which are directly usable, i.e. which are readily dilutable with water and may be directly metered into the treatment drum, if desired.

The invention thus further provides a process for the production of fat-liquored, tanned leather or pelt, comprising the steps of fat-liquoring and tanning, wherein an animal hide, skin or pelt is fat-liquored with substituted acylaminopolyorganosiloxane (A) in the presence of a surfactant or surfactant mixture (B) defined above before, during or/and after tanning.

As a substrate for the fat-liquoring treatment with substituted acylaminopolyorganosiloxane (A) there may be used any conventional animal hides, skins and pelts as are in general employed for fat-liquoring, e.g. hides from cow, calf or buffalo (e.g. also as split hides), skins from goat, sheep or pig, buckskins and pelts; but also other hides and skins e.g. from other mammals (foal, wild boar, camel, lama, kangaroo, wallaroo, wallaby), reptiles (snakes, lizards), fishes (shark) or birds (ostrich), woolled skins and furskins, before tanning or that have been tanned in any conventional way and which may have optionally been defatted before tanning, as is mostly done e.g. for sheepskins, pigskins or wild boar skins. They may be or have been tanned with cationic metal compounds of tanning activity, in particular with polybasic metal compounds, mainly chromium, aluminium, iron, zirconium or titanium salts (e.g. sulphates, chlorides, formates, acetates, oxalates, nitrates), or with non-metal tanning agents e.g. vegetable tanning agents, aldehydic tanning agents, polymers, resins or heterocyclic tanning agents. As heterocyclic tanning agents there may be mentioned in particular halogen-substituted di- or triazines containing an aromatic carbocyclic ring and a sulpho group, or halogen-substituted di- or triazines containing a vinylsulphone group or vinylsulphone precursor group (β-sulphato-, β-phosphato- or β-chloro-ethylsulphone) linked to an aromatic carbocyclic, araliphatic or aliphatic bridging group and preferably containing a sulpho group (e.g. the triazinic compounds described in WO-2010/130311 A1).

If desired a further non-mineral tanning agent of anionic or/and ethylenically unsaturated character or/and containing groups of basic character may be applied for pre-tanning before a main tanning, or in combination with a heterocyclic tanning agent in a main or full tanning, or/and preferably for a complementary tanning after a main or full tanning with a heterocyclic tanning agent, or even for retanning.

These further non-mineral tanning agents preferably are
vegetable tanning agents,
syntans,
synthetic, semisynthetic or natural resins or polymers, or/and
tanning natural oils or modified oils.

As vegetable tanning agents there may be employed known vegetable tanning agents, in particular pyrogallol- or pyrocatechin-based tannins, e.g. valonea, mimosa, ten, tara, oak, pinewood, sumach, quebracho and chestnut.

As syntans there may be employed known synthetic tanning agents, in particular syntans derived from sulphonated phenols and/or naphthols, and/or sulphones or polymers of sulphones and/or sulphonated phenols and/or sulphonated naphthols with formaldehyde or acetaldehyde and optionally urea, among which sulphone-based products are preferred.

As tanning synthetic or semisynthetic or natural resins or polymers there may be employed e.g. known polyacrylates, polymethacrylates, copolymers of maleic anhydride and styrene, condensation products of formaldehyde with melamine or dicyandiamide, lignins and natural flours. Among the synthetic or semisynthetic or natural resins or polymers those of anionic character (polyacrylates, polymethacrylates, lignin sulphonates and copolymers of maleic anhydride and styrene) and which are free of basic amino groups are particularly worth mention.

As tanning natural or modified oils there may be employed known natural triglycerides, e.g. rape seed oil, fish oils or their oxidised derivatives, sulphated, sulphonated or oxy-sulphited fish oils, or their oxidised derivatives, or surrogates thereof.

Tanning with a heterocyclic tanning agent may be carried out as a full tanning, or as a pre-tanning before a non-metal main tanning, which may be carried out with a vegetable tanning agent or with a synthetic tanning agent other than heterocyclic—e.g. as mentioned above—or also with a heterocyclic tanning agent, or as a main tanning after a non-metal or even non-mineral pre-tanning (which may be vegetable or synthetic) e.g. carried out with one or more of the non-metal and non-heterocyclic tanning agents mentioned above. Where the tanning with a heterocyclic tanning agent is carried out as a main tanning subsequently to a vegetable pre-tanning or to a synthetic pre-tanning with syntans, the pH may if required be adjusted to the desired value between 6 and 10, e.g. by addition of an alkali metal carbonate, bicarbonate or formate for the tanning with the heterocyclic tanning agent.

According to a particular feature the heterocyclic tanning agent may be used in combination with another non-mineral tanning agent, i.e. a vegetable tanning agent or a syntan or an anionic tanning resin or polymer, e.g. in a weight ratio of heterocyclic tanning agent to the other non-mineral tanning agent in the range of 1/20 to 20/1, more particularly 2/1 to 10/1. The concentration of the combined tanning agents may be as desired for achieving a defined tanning, e.g. in the range of 0.5 to 20%, preferably 1 to 10% referred to the fleshed weight of the substrate.

According to a further particularly preferred feature of the invention, the substrates are first tanned in one or two stages with a heterocyclic tanning agent and then are subjected to a complementary tanning with a non-mineral and non-heterocyclic tanning agent, which preferably is a vegetable tanning agent, a syntan or a tanning anionic resin or polymer. As a complementary tanning there is intended here an additional tanning step carried out after main or full tanning with a heterocyclic tanning agent, and which substantially does not modify the characteristic kind of properties of the leather, skin or pelt tanned with the heterocyclic tanning agent, but may improve some of the typical tannage properties. Typically it is carried out with a minor proportion of the complementary tanning agent, referred to the proportion of the employed main or full heterocyclic tanning agent, e.g. 5 to 80%, preferably 10 to 60%, of the employed proportion of heterocyclic tanning agent. This complementary tanning may advantageously be carried out sequentially to the tanning with the heterocyclic tanning agent under temperature conditions as mentioned above, e.g. 10 to 40° C., at bath lengths preferably as used for tanning with the heterocyclic tanning agent, e.g. in the range of 40 to 200%, and under pH conditions as resulting from the tannage with the heterocyclic tanning agent, preferably after rinsing with water, usually this pH may range in the scope of 4 to 7.

Complementary tanning with the above non-mineral and non-heterocyclic tanning agents may be carried out in the tannery directly after tanning, or even after having rinsed, dried and optionally mechanically treated the tanned leather, skin or pelt.

If the fat-liquoring of the invention is carried out before tanning, it may be carried out e.g. after pickling or, if a depickling has been carried out, optionally after depickling, or, if no pickle is carried out, after bating.

Tanning with the mentioned heterocyclic compounds is expediently carried out under the conditions described in WO-2010/130311 A1, in particular on the bated substrate or on a pickled and depickled substrate in an aqueous tanning bath the pH of which at the beginning of tanning is in the range of 6 to 10. Complementary tanning with the mentioned non-heterocyclic non-mineral tanning agents is expediently also carried out under the conditions described in WO-2010/130311 A1.

The bated substrates (animal hides, skins or pelts) may have been processed in the beamhouse before tanning, i.e. trimmed, soaked, limed, delimed and bated in conventional way. Before deliming the limed hides, skins or pelts are usually fleshed and, if required, split and optionally scudded, shaved etc. and, if required, defatted and/or dehaired.

Bated hides, skins and pelts to be used as substrates in the process of the invention may have been produced in conventional way, in the beamhouse, in particular by deliming the limed substrates and bating, using known agents for each of the mentioned processing steps.

Deliming may have been carried out in conventional way with known compounds mainly acids, ammonium salts of low molecular aliphatic carboxylic acids, ammonium sulphate or sodium phosphate. Optionally the deliming composition may contain an enzyme e.g. as mentioned below, so that, if desired, bating and deliming may at least in part be combined.

For bating there may be employed known proteolytic bates, in particular in the form of bating compositions based on conventional proteolytic enzymes, mainly bacterial proteases, fungal proteases, and pancreas enzyme. Occasionally also other enzymes may be employed, such as lipases, amylases and also other hydrolases. Pancreas enzyme alone or in admixture with other enzymes (e.g. lipases, amylases and also other hydrolases) is preferred. Commercial forms of such enzymes may be formulated together with other components, especially with some mineral carriers, saccharides or polysaccharides and/or a hydrotrope. For the purpose of the invention substrates conventionally bated with bating compositions based on pancreas enzyme are well suitable.

The above bating compositions are in particular of an optimum activity in the weakly basic pH range, more particularly at a basic pH≤11, and consequently the pH of the bated substrate is preferably in the weakly basic range, in particular a pH in the range of 7.5 to 11, more preferably 7.5 to 10.

Where the substrate has been delimed with acids, also acidic bates may be used, e.g. pepsins e.g. in the form of a solution of 2% pepsin in water and at a pH in the range of 3-4.

Where the bated substrate is directly fat-liquored with substituted acylaminopolyorganosiloxane (A) or respectively with composition (F), its pH may be adjusted to the suitable value in the range of pH 3-8, or preferably 4-8 or more preferably 4.5-7.5 as mentioned above, by treatment with acids or bases, e.g. those mentioned above under (C4), as may be required. The substrate may have been pickled (e.g. to a pH in the range of 2 to 5) and optionally depickled (e.g. to a pH in the range of 6 to 8).

Tanning may be or have been carried out in one or more steps, namely as a full tanning or as a pre-tanning followed by a main tanning, or as a main tanning followed by a retanning, or as a pre-tanning followed by a main tanning and a retanning. Where tanning is carried out with a heterocyclic tanning agent, a complementary tanning may also be carried out after main tanning. The fat-liquoring process with substituted acylaminopolyorganosiloxane (A) may be carried out after a full or main tanning, or after a pre-tanning before a main tanning, or after a main tanning and before a retanning, or after a retanning or even before a full tanning or before a pre tanning. If a complementary tanning is carried out, the fat-liquoring process with substituted acylaminopolyorganosiloxane (A) may be carried out before or preferably after complementary tanning. Preferably the fat-liquoring process with substituted acylaminopolyorganosiloxane (A) is carried out after a pre-tanning or, more preferably, after a full or main tanning and optionally a complementary tanning (if main tanning was carried out with a heterocyclic tanning agent) and/or a retanning, or stepwise after a pre-tanning and after a main tanning and optionally a complementary tanning (if main tanning was carried out with a heterocyclic tanning agent) and/or optionally a retanning. Fat-liquoring with substituted acylaminopolyorganosiloxane (A) in the presence of surfactant or surfactant mixture (B) or preferably with composition (F) comprising surfactant or surfactant mixture (B) may even be carried out in place of a conventional retanning, since the fat-liquoring compositions (F), especially in the form of (F) preferably with substituted acylaminopolyorganosiloxane (A) in combination with (B3) or with (B3) and (B6) and/or (B2), have also retanning properties, so as to provide a kind of "fat retannage".

If desired, the tanned leather or pelt may also be dyed before fat-liquoring with substituted acylaminopolyorganosiloxane (A) or even before and after fat-liquoring with (A).

The fat-liquoring treatment of the hides, skins and pelts with substituted acylaminopolyorganosiloxane (A) may be carried out under mild acidic to weakly basic, preferably weakly acidic to nearly neutral pH-conditions, suitably in an aqueous bath at a pH in the range of 3 to 8, preferably 4 to 8, more preferably 4.5 to 7.5. The bath may be of a length as conventional per se for fat liquoring, e.g. in the range of 50 to 300% by weight referred to the wet weight of the substrate. Satisfactory fat-liquoring may already be achieved with low concentrations of substituted acylaminopolyorganosiloxane (A), e.g. at concentrations in the range of 0.4 to 8% of (A), preferably 0.8 to 4% of (A), referred to the wet weight of the substrate. The temperature may vary in a broad range, e.g. in the range of 15 to 70° C., preferably 30-60° C. The treatment time may vary in a broad range e.g. from 30 minutes to 3 hours, preferably 1-2 hours. Depending e.g. on the kind and quality of the substrate and on the tanning there may be chosen preferred parameters for the treatment with substituted acylaminopolyorganosiloxane (A).

If desired, in particular in view of the fat-liquoring effect aimed at, further fat-liquoring agents (G) may be included in the fat liquoring bath or even in (F). As (G) are suitable in particular organic fat-liquoring agents, e.g.
1) natural, i.e. vegetable or animal, fat-liquoring agents,
2) modified, especially sulphated, sulphited or oxy-sulphated fats or oils (most preferably reclaimed edible oils aerated and sulphated),
3) synthetic fat-liquoring agents, e.g. polymers preferably containing sulphosuccinate groups.

Expediently fat-liquoring agent (G), if employed, is present in a minor proportion with reference to substituted acylaminopolyorganosiloxane (A), e.g. up to 70% by weight of (A), preferably up to 50%, more preferably up to 30% by weight of (A). If fat-liquoring agent (G) is present together with substituted acylaminopolyorganosiloxane (A), it is preferably present in a ratio of 2 to 70%, more preferably 5 to 50%, especially 5 to 30% by weight referred to the weight of (A). Most preferably (A) is employed without any admixture of (G).

After the fat-liquoring treatment with substituted acylaminopolyorganosiloxane (A) in the presence of surfactant or surfactant mixture (B), optionally in the form of composition (F) comprising also (B), the leathers or pelts may be further treated in a manner conventional per se, e.g. washed or rinsed and may be dyed and finished mechanically, e.g. staked, sammied or even shaved, or/and may be finished with conventional finishing agents.

By means of the process of the invention there are obtainable fat-liquored leathers and pelts, especially a full fat-liquoring or through-fat-liquoring, of high quality and outstanding properties, mainly penetration, feel (suppleness, softness, fullness, firmness), tensile properties (tensile strength, tear load, pliability), grain structure, hydrophilicity, water vapour permeability, fastnesses (light fastness, heat resistance, dry heat resistance), and satisfactory shelf life, and without any fatty spew or stain formation—while fogging can be kept to a minimum.

The kind and quality of the fat-liquoring may further be optimised depending on the kind and quality of the tannage in the substrate. Thus for mineral tanning, especially chrome tanning, polysiloxanes (A) with a lower degree of sulphitation, preferably in the range of 20-70%, especially 20-50%, are preferred with a view to soft and supple feel of the leather or pelt, whereas polysiloxanes (A) with a higher degree of sulphitation, preferably in the range of 50-100%, especially 70-100%, are preferred with a view to fullness and firmness of the leather or pelt. For non-mineral tanning, especially with heterocyclic tanning agents described in WO-2010/130311 A1, in particular of formula

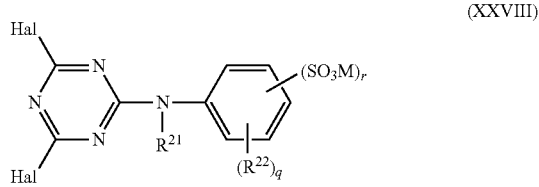

(XXVIII)

wherein
Hal signifies fluorine or chlorine,
$R^{21}$ signifies hydrogen, $C_{1-8}$-alkyl or $-(C_{2-3}$-alkylene-O$)_s$-H,
$R^{22}$ signifies $C_{1-4}$-alkyl or alkoxy,
q signifies 0 or 1,
r signifies 1 or 2,
s signifies 1 to 10 and
M signifies hydrogen, an alkali metal cation or a quaternary ammonium cation, among which are preferred those in which Hal is chlorine, $R^{21}$ is hydrogen, q is 0 and M is sodium, there are obtainable with any degree of sulphitation, in particular in the range of 20 to 100%, preferably 40-80%, an outstanding soft and supple feel and also a satisfactory fullness and firmness.

Due to the optimum penetration of substituted acylaminopolyorganosiloxane (A) into the substrate the fat liquoring is optimally distributed throughout the leather structure. Further mechanical treatments such as staking or shaving may thus be carried out without having to fear any damage of the fat liquored tanned hides, skins or pelts.

There may be treated very thin leathers (e.g. book binders leather, glove leather, garment leather), medium strength leather (e.g. upholstery leather, shoe upper leather, trunk leather, leather for hand bags and suitcases) and thick leathers (e.g. leathers for sport articles, harness, belts or saddlery).

They are particularly suitable for automotive upholstery in view of their satisfactory hydrophilicity, water vapour permeability and air permeability and optimal light and heat fastnesses (light fastness, heat resistance, dry heat resistance) and low fogging.

In the following Examples percentages are by weight. In Application Example A percentages refer to the wet weight of the substrate if not otherwise indicated; in Application Examples Ba), Bb) and Bc) percentages refer to the weight of the split substrate, if not otherwise indicated; in Application Example Bd) percentages refer to the weight of the split and shaved substrate, if not otherwise indicated. The dyes are in commercial form blended with sodium chloride, with a dye content of around 60%, "C.I." stands for "Colour Index".

Example 1

Surfactant (B21)

In a reactor (closed vessel which is fitted with an overhead stirrer, a condenser, a dropping funnel and a thermometer) are given 219 g of oleic acid, 155 g of polyethylene glycol 200 and 1.5 g of p-toluenesulphonic acid are added with stirring. The reaction mixture is heated to 95-100° C. and vacuum is applied to reach a residual pressure of 67-93 mbar in the vessel. These conditions are maintained for 3-3.5 hours removing 14 g of water. At this point the acidity assessed by titration is 7 mg KOH/g. The reaction mixture is then cooled to 80-90° C. and 38 g of maleic anhydride are added. The temperature is maintained at 88-92° C. for 30-40 minutes, then the reaction mixture is heated to 100-110° C. and maintained at this temperature for 3 hours. The reaction mixture is then heated to 120-130° C. and maintained at this temperature for 2-3 hours, under vacuum (80-93 mbar), removing 7 g of water. At this point the acidity assessed by titration is 14 mg KOH/g.

Example 2

Aminosilicone (S1)

In a closed vessel which is fitted with an overhead stirrer, a condenser, a dropping funnel and a thermometer are given 174 g of α,ω-(dihydroxy)-polydimethylsiloxane, 59 g of N-[3-(dimethoxy methyl silyl)propyl]ethylene diamine, 174 g of octamethylcyclotetrasiloxane and 1.1 g of tetrabutylammonium hydroxide. This mixture is slowly heated with stirring and under a mild nitrogen flow within 1.5 hour to 70° C. and stirring is continued at this temperature for 4 hours. Then the reaction mixture is heated within 1.5 hour to 120° C. in order to destroy the catalyst, then cooled to 25-30° C. and heated again to 120° C. At this temperature vacuum is applied to give a residual pressure of 40-53 mbar. At this point the mixture is heated within 1.5 hour to 150° C. and maintained at 150° C. and 40 mbar for 1.5 h removing 47 g of siliconic short chains and by-products. There is obtained an aminopolyorganosiloxane [aminosilicone (S1)] with an amine number of 1.45 meq/g, assessed by titration, and average molecular weight $\overline{M}_W$ of 1000 assessed by gas permeation chromatography (GPC). Aminosilicone (S1) thus is composed of 72.5% of polydimethylsiloxane with 3-[(2-aminoethyl)amino]propyl-(methyl)siloxy units and 27.5% of polydimethylsiloxane without 3-[(2-aminoethyl)amino]propyl-(methyl)siloxy units.

Example 3

Acylaminosilicone (A1)

320 g of aminosilicone (S1) produced according to Example 2, are charged into a reactor, 100 ml of tetrahydrofuran are added and the mixture is heated to 40° C. with stirring 48 g of maleic anhydride are added and stirring is continued at 40° C. for 30 minutes. After 40 minutes the acidity is determined by titration with a 0.5M aqueous sodium hydroxide solution. The carboxylate number is 1.04 meq/g. An aqueous solution of 45.6 g of sodium metabisulphite and 30.4 g of aqueous 30% sodium hydroxide in 100 g of water is added with stirring and stirring is continued for 20 minutes, then 250 g of water are added and the mixture is heated to 60° C. under a nitrogen flow, removing the tetrahydrofuran. There is obtained a paste with a dry substance content of 48.6%. The degree of sulphitation is 90% referred to the maleic anhydride (by titration of the non-reacted sodium bisulphite, as $NaHSO_3$), and the sulphonate number is 1.207 meq/g, referred to 1 g of (S1).

Example 4

Composition (F1)

300 g of diester (B21) produced according to Example 1 are given into a reactor and heated to 60-70° C. with stirring. 37.5 g of maleic anhydride are added and stirring is continued for 15 minutes at this temperature. 270 g of aminosilicone (S1) produced in Example 2 are added and stirring is continued for 70 minutes. At this point the acidity is determined by titration with a 0.5M aqueous sodium hydroxide solution: The carboxylate number is 0.7 meq/g. 300 g of water is added and the mixture is heated to 80-90° C. A solution of 63 g of sodium metabisulphite and 42 g of an aqueous 30% sodium hydroxide solution in 155 g of water is added with stirring over 30 minutes and stirring is continued at 80-90° C. The —$SO_3^-$ content is 1.3% referred to the weight of the reaction product. The degree of sulphitation referred to maleic anhydride is 75%, and the sulphonate number is 1.04 meq/g referred to 1 g of (S1). 650 g of water, 47 g of aqueous 30% sodium hydroxide solution, 67 g of oleoylsarcosine and 4 g of NIPACIDE® BIT 20 (a commercial biocide based on 1,2-benzothiazolin-3-one of Nipa LAB's Ltd., from Nipa Laboratorien GmbH, Germany) are added with stirring, and stirring is continued until a homogeneous dispersion is obtained.

Example 5

Composition (F2)

Into a reactor are given 150 g of the paste produced in Example 3, 76 g of water, 90 g of diethyleneglycol monobutylether, 38 g of an aqueous 30% sodium hydroxide solution and 38 g of sodium dodecylbenzenesulphonate and the mixture is stirred until a homogeneous dispersion is obtained.

Example 6

Composition (F3)

107 g of stearic acid are given into a reactor. 75 g of polyethylene glycol and 0.7 g of sulphuric acid (of 98% concentration) are added with stirring and the mixture is heated to 95-100° C. and vacuum is applied to reach a residual pressure of 67-93 mbar in the vessel. These conditions are maintained for 3-3.5 hours removing 6.5 g of water. At this point the acidity assessed by titration is 2.7 mg KOH/g. The reaction mixture is then cooled to 80-90° C. and 18.5 g of maleic anhydride are added. The temperature is maintained at 88-92° C. for 30-40 minutes (acidity=49 mg KOH/g), then the reaction mixture is heated during 50-60 minutes to 100-110° C. and maintained at this temperature for 3 hours. The reaction mixture is then heated to 120-130° C. and maintained under vacuum (80-93 mbar) at this temperature for 2-3 hours, removing 3 g of water. At this point the acidity, determined by titration, is 16.5 mg KOH/g. The mixture is then cooled to 60-70° C., 24 g of maleic anhydride are added with stirring and stirring is continued at this temperature for 15 minutes, then 173.2 g of aminosilicone (S1) produced in Example 2 are added and stirring is continued for 70 minutes. At this point the acidity is determined by titration with an aqueous 0.5M sodium hydroxide solution. The carboxylate number of the mixture is 0.79 meq/g. 190 g of water are added and the mixture is heated to 80-90° C. A solution of 40 g of sodium metabisulphite and 27 g of an aqueous 30% sodium hydroxide solution in 100 g of water is added with stirring over 30 minutes and stirring is continued at 80-90° C. for 50-60 minutes. The —$SO_3^-$ content referred to the reaction product mass is 1.17%. The sulphonate number is 0.8699 meq/g, referred to (S1). 250 g of water, 23 g of an aqueous 30% sodium hydroxide solution and 4 g of NIPACIDE® BIT 20 are added with stirring and stirring is continued until a homogeneous dispersion is obtained. (pH=7.6. dry substance content=40.0%)

Example 7

Cylaminosilicone (A2)

101.8 g of aminosilicone (S1) produced according to Example 2, are charged into a reactor, 50 ml of tetrahydrofuran are added with stirring and the mixture is heated to 70° C. with stirring. 15 g of maleic anhydride are added and the temperature increases to 80° C.; stirring is continued for 30 minutes. The acidity is determined by titration with a 0.5M aqueous sodium hydroxide solution. Carboxylate value 0.93 meq/g. 113 g of diester [Surfactant (B21)] produced in Example 1 and 113 g of water are added with stirring. At 60° C. a solution of 18 g of sodium metabisulphite and 12 g of an aqueous 30% sodium hydroxide solution in 58 g of water is added with stirring, and stirring is continued for 50-60 minutes. The —$SO_3^-$ content of the reaction product mass is 0.7%, the sulphonate number is 0.374 meq/g referred to (S1). Then the mixture is heated to 60° C. under a nitrogen flow to remove tetrahydrofuran. At the end of distillation 70 g of water are added. There is obtained a paste with a dry substance content of 47.9% and a pH of 5.7.

Example 8

Surfactant (B22)

196 g of oleic acid are given into a reactor. 139 g of polyethylene glycol 200 and 1.3 g of methanesulphonic acid are added with stirring and the mixture is heated to 90-105° C. and vacuum is applied to reach a residual pressure of 67-93 mbar in the vessel. These conditions are maintained for 3-3.5 hours removing 12.5 g of water. The reaction mixture (323.8 g) is then cooled to 80-90° C. and 34.1 g of maleic anhydride is added. A weakly exothermic reaction takes place, then the temperature is maintained at 88-92° C. for 30-40 minutes and then the reaction mixture is heated during 50-60 minutes to 100-110° C. with vacuum (residual pressure 67-80 mbar) and maintained at this temperature for 3 hours while condensation water is distilled. The reaction mixture is then heated to 120-130° C. and maintained at this temperature for 2-3 hours, continuing distillation. 6.3 g of water are distilled. Yield 351.6 g.

Example 9

Surfactant (B32)

351.6 g of the product of Example 8 are given into a reactor and heated to 80-90° C. An aqueous solution of 33 g of sodium metabisulphite and 27.5 g of an aqueous 30% NaOH solution in 88 g of water is added with stirring and the mixture is heated to 85-98° C. and stirring is continued at this temperature for 2-3 hours. (—$SO_3^-$%=3.8%).

Example 10

Acylaminosilicone (A3)

201 g of aminosilicone (S1) produced according to Example 2 and 100 g of tetrahydrofuran are charged into a reactor, and the mixture is heated to 40° C. with stirring. 30 g of maleic anhydride is added and stirring is continued at 40° C. for 30 minutes. After 40 minutes the acidity is determined by titration with an aqueous 0.5M sodium hydroxide solution. Carboxylate value 1.01 meq/g. An aqueous solution of 9.4 g of sodium metabisulphite and 6.3 g of an aqueous 30% sodium hydroxide solution in 23 g of water is added with stirring and stirring is continued for 15-20 minutes at 35-40° C. There is obtained a paste with a dry substance content of 72% and residual bisulphite=0.63 g. Molar sulphitation yield=31% (referred to moles of maleic anhydride, by titration of the non-reacted sodium bisulphite, as $NaHSO_3$). Sulphonate number=0.412 meq/g referred to 1 g of (S1).

Example 11

Acylaminosilicone (A4)

320 g of aminosilicone (S1) produced according to Example 2 and 100 g of tetrahydrofuran are charged into a reactor, and the mixture is heated to 40° C. with stirring. 47 g of maleic anhydride is added and stirring is continued at 40° C. for 30 minutes. After 40 minutes the acidity is determined by titration with an aqueous 0.5M sodium hydroxide solution: Carboxylate number 1.01 meq/g. An aqueous solution of 30 g of sodium metabisulphite and 20 g of an aqueous 30% sodium hydroxide solution in 80 g of water is added with stirring and stirring is continued for 80-90 minutes at 35-40° C. There is obtained a paste with a dry substance content of 68%, residual bisulphite=1.36 g. Molar sulphitation yield=62.8%. referred to the maleic anhydride (by titration of the residual non-reacted sodium bisulphite, as $NaHSO_3$). Sulphonate number=0.821 meq/g referred to 1 g of (S1).

Example 12

Composition (F4)

216 g of the product of Example 10 containing Acylaminosilicone (A3), 200 g of the product of Example 9, 33 g of oleoylsarcosine and a quantity of aqueous 30% sodium hydroxide to reach a pH of 6.5 are charged into a reactor. 400 g of water are added and tetrahydrofuran is eliminated by distillation under reduced pressure (125 mbar). Then water is added to reach a dry substance content of 40.2%.

Example 13

Composition (F5)

244.2 g of the product of Example 11 containing Acylaminosilicone (A4), 200 g of the product of Example 9, 33 g of oleoylsarcosine and a quantity of aqueous 30% sodium hydroxide solution to reach a pH of 7.0 are charged into a reactor. 400 g of water are added and tetrahydrofuran is eliminated by distillation under reduced pressure (125 mbar). Then water is added to reach a dry substance content of 40.0%.

Example 14

Composition (F6)

100 g of tallow amine are charged into a reactor, 100 g of aminosilicone (S1) produced according to Example 2 are added with stirring, and the mixture is heated to 80-85° C. with stirring. At this temperature 52 g of maleic anhydride are added and stirring is continued at 80° C. for 90 minutes. The acidity is determined by titration with an aqueous 0.5M sodium hydroxide solution: Carboxylate number 2.2 meq/g. 100 g of water and 21 g of sodium hydroxide are added and the mixture is heated to 80-85° C. with stirring. A solution of 51 g of sodium metabisulphite and 33 g of an aqueous 30% sodium hydroxide solution in 150 g of water is added over 30 minutes with stirring and stirring is continued for 90 minutes at 80-85° C. Then the $—SO_3^-$ content is determined by titration of the residual sulphite content (residual sodium sulphite=3.85%, sulphonate ion content 0.15%, molar sulphitation yield=55%). 30 g of oleoyl sarcosine, 150 g of water and sodium hydroxide to give a pH of 6.2 are added. There is obtained an aqueous composition with a dry substance content of 40.5%.

Example 15

Aminosilicone (S2)

In a closed vessel which is fitted with an overhead stirrer, a condenser, a dropping funnel and a thermometer are given 200 g of α,ω-(dihydroxy)-polydimethylsiloxane, 100 g of N-[3-(dimethoxy methyl silyl)propyl]ethylene diamine, 200 g of octamethylcyclotetrasiloxane and 1.3 g of tetrabutylammonium hydroxide. This mixture is slowly heated with stirring and under a mild nitrogen flow within 1.5 hour to 70° C. and stirring is continued at this temperature for 4 hours. Then the reaction mixture is heated within 1.5 hour to 120° C. in order to destroy the catalyst, then cooled to 25-30° C. and heated again to 120° C. At this temperature vacuum is applied to give a residual pressure of 40-53 mbar. At this point the mixture is heated within 1.5 hour to 150° C. and maintained at 150° C. and 40-53 mbar for 1.5 h removing 50 g of siliconic short chains and by-products. There is obtained an aminopolyorganosiloxane [aminosilicone (S2)] with an amine number of 2.2 meq/g, determined by titration.

Example 16

Composition (F7)

In a reactor are charged 150 g of Surfactant (B21) of Example 1, and heated with stirring to 60-70° C. 29 g of maleic anhydride are added an stirring is continued for 15 minutes at 60-70° C., then 136 g of Aminosilicone (S2) of Example 15 are added. The acidity is determined by titration with an aqueous 0.5M sodium hydroxide solution: Carboxylate number 0.97 meq/g. 150 g of water is added and the mixture is heated to 80-90° C. with stirring. A solution of 33 g of sodium metabisulphite and 22 g of an aqueous 30% sodium hydroxide solution in 150 g of water is added over 30 minutes with stirring and stirring is continued for 90 minutes at 80-90° C. Then the $—SO_3^-$ content is determined by titration of the residual sulphite content (sulphonate ion content 0.87%). 200 g of water, 25 g of an aqueous 30% sodium hydroxide solution, 33.5 g of oleoyl sarcosine and 4 g of NIPACIDE® BIT 20 are added with stirring to give an aqueous homogeneous composition.

Example 17

Aminosilicone (S3)

Example 15 is repeated, with the difference that instead of 100 g of N-[3-(dimethoxy methyl silyl)propyl]ethylene diamine there are employed 160 g thereof. There is obtained an aminopolyorganosiloxane [aminosilicone (S3)] with an amine number of 3.2 meq/g, determined by titration. The siliconic short chains and by-products removed by distillation at 150° C. and 40-53 mbar are 116 g.

Example 18

Composition (F8)

Example 16 is repeated, with the difference that instead of 29 g of maleic anhydride there are employed 42.6 g thereof, and instead of Aminosilicone (S2) there is employed the same quantity of Aminosilicone (S3). The carboxylate number of the intermediate addition product with maleic anhydride is 1.2 meq/g. After reaction with the sodium metabisulphite the sulphonate ion content is 0.9%. Upon addition of the 200 g of water, 25 g of aqueous 30% sodium hydroxide solution, 33.5 g of oleoyl sarcosine and 4 g of NIPACIDE® BIT 20 with stirring, there is obtained an aqueous homogeneous composition.

Example 19

Aminosilicone (S4)

Example 15 is repeated, with the difference that instead of 100 g of N-[3-(dimethoxy methyl silyl)propyl]ethylene diamine there are employed 117.6 g of N-[3-(trimethoxy silyl)propyl]amine. There is obtained an aminopolyorganosiloxane [aminosilicone (S4)] with an amine number of 1.496 meq/g, determined by titration. The siliconic short chains and by-products removed by distillation at 150° C. and 40-53 mbar are 113.6 g.

Example 20

Composition (F9)

In a reactor are charged 120 g of Surfactant (B21) of Example 1, and heated with stirring to 60-70° C. 16.1 g of maleic anhydride are added an stirring is continued for 15 minutes at 60-70° C., then 110 g of Aminosilicone (S4) of Example 19 is added. The acidity is determined by titration with an aqueous 0.5M sodium hydroxide solution: Carboxylate number 0.86 meq/g. A solution of 25.6 g of sodium metabisulphite and 17 g of an aqueous 30% sodium hydroxide solution in 214 g of water is added over 30 minutes with stirring and heating to 80-85° C. and stirring is continued for 90 minutes at 80-85° C. Then the $—SO_3^-$ content is 1.3% referred to the reaction product mass. The degree of sulphitation referred to maleic anhydride is 75%, and the sulphonate number is 1.27 meq/g referred to 1 g of (S4). 247 g of water, 23 g of an aqueous 30% sodium hydroxide solution, 27.4 g of oleoyl sarcosine and at 22° C. 1.6 g of NIPACIDE® BIT 20 are added with stirring to give an aqueous homogeneous composition (yellow paste of pH 6.7 and dry substance content of 38.6%).

Example 21

Aminosilicone (S5)

In a closed vessel which is fitted with an overhead stirrer, a condenser, a dropping funnel and a thermometer are given 200 g of α,ω-(dihydroxy)-polydimethylsiloxane, 50 g of N-[3-(trimethoxysilyl)propyl]diethylene triamine, 200 g of octamethylcyclotetrasiloxane, 300 g of tetrahydrofuran and 1.3 g of tetrabutylammonium hydroxide. This mixture is slowly heated with stirring and under a mild nitrogen flow within 1.5 hour to 70° C. and stirring is continued at this temperature for 4 hours. Then the reaction mixture is heated within 1.5 hour to 120° C. in order to destroy the catalyst and remove the tetrahydrofuran, then cooled to 25-30° C. and heated again to 120° C. At this temperature vacuum is applied to give a residual pressure of 40-53 mbar. At this point the mixture is heated within 1.5 hour to 150° C. and maintained at 150° C. and 40-53 mbar for 1.5 h removing 70 g of siliconic short chains and by-products. There is obtained an aminopolyorganosiloxane [aminosilicone (S5)] with an amine number of 1.6 meq/g, determined by titration.

Example 22

Composition (F10)

In a reactor are charged 120 g of Surfactant (B21) of Example 1, and heated with stirring to 60-70° C. 17.6 g of maleic anhydride are added an stirring is continued for 15 minutes at 60-70° C., then 110 g of Aminosilicone (S5) of Example 21 is added. The acidity is determined by titration with an aqueous 0.5M sodium hydroxide solution: Carboxylate number 0.70 meq/g. A solution of 28 g of sodium metabisulphite and 18.6 g of an aqueous 30% sodium hydroxide solution in 220 g of water is added over 30 minutes with stirring and heating to 80-85° C. and stirring is continued for 90 minutes at 80-85° C. Then the $—SO_3^-$ content is 1.1% referred to the reaction product mass. The degree of sulphitation referred to maleic anhydride is 76%, and the sulphonate number is 1.37 meq/g referred to 1 g of (S5). 250 g of water, 25 g of an aqueous 30% sodium hydroxide solution, 30 g of oleoyl sarcosine and at 22° C. 1.64 g of NIPACIDE® BIT 20 are added with stirring to give an aqueous homogeneous composition (yellow paste of pH 6.2 and dry substance content of 39%).

Application Example A

A wet blue calf leather (Spain, weight category 30 kg), shaved to 1.2-1.3 mm thickness is charged into a drum. 200% of water at 35° C., 0.5% of defatting agent ($C_{12-15}$-alkanol ethoxylated with 7 mols of ethylene oxide per mol of alkanol) and 0.5% of acetic acid are added, the drum is switched on and drumming is carried on for 30 minutes. The bath is drained off. 100% of water at 35° C., 2% of sodium formate and 0.5% of sodium bicarbonate are added and drumming is continued for 60 minutes. The pH of the cross section is uniformly 5.0. The bath is drained off. 200% of water at 35° C. is added and drumming is carried on for 5 minutes. Then the bath is drained off. 100% of water at 35° C. and 5% of a retanning syntan based on sulphomethylated dihydroxydiphenylsulphone reacted with formaldehyde and 5% of a phenolic syntan (reaction product of sulphonated phenol with formaldehyde and urea) are added and drumming is carried on for 60 minutes. 3% of the black dye C.I. Acid Black 210 is added and drumming is continued for 1 hour, then 200% of water at 50° C. and 1.5% of formic acid are added and drumming is continued for 30 minutes, then the bath is drained off. 200% of water at 50° C. is added and drumming is carried on for 5 minutes. Then the bath is drained off. 100% of water at 50° C. and 10% of the fat-liquoring composition (F1) of Example 4 are added and drumming is carried on for 60 minutes. 0.5% of formic acid is added and drumming is continued for 20 minutes, then the bath is drained off. 200% of water at 18° C. are added and drumming is carried on for 5 minutes. Then the bath is drained off. The leather is discharged, sammied, vacuum dried at 70° C. during 3 minutes, dried hanging, staked and conditioned. There is obtained a fat-liquored, black dyed leather of satisfactory properties, in particular penetration, tensile properties, feel, hydrophilicity, air and vapour permeability, and fastnesses and substantially non-fogging.

Application Example B

Application Example A is repeated, with the difference that instead of the chrome tanned leather (spanish wet blue calf leather of the weight category 30 kg) there is employed a bovine tanned leather tanned as follows:

a) Deliming and Bating:

Bovine limed hide (Swiss bull hide of the weight category 30 kg), fleshed and split to a thickness of 2.4-2.6 mm is charged into a drum with 200% of water at 25° C., 0.1% of defatting agent ($C_{12-15}$-alkanol ethoxylated with 7 mols of ethylene oxide per mol of alkanol) and 0.2% of an ammonium based deliming agent (ammonium chloride and ammonium sulphate) and drummed for 20 minutes. Then the bath is drained, a fresh bath of 50% of water at 35° C., 0.1% of the above mentioned defatting agent and 0.5% of the above mentioned ammonium based deliming agent is charged into the drum and drumming is continued for 15 minutes. A further 0.5% of ammonium based deliming agent and 0.8% of a mixture of 70% boric acid and 30% mixed organic acids (adipic, glutaric and succinic acids in even parts) are added and drumming is carried on for 90 minutes. 0.6% of Feliderm® Bate PB1 p (a pancreas enzyme based bate of Clariant, Switzerland) is added and drumming is continued for 30 minutes and then the bath is drained. 300% of water is added and drumming is carried on for 15 minutes at 35° C. then the bath is drained.

b) Tanning:

A fresh bath of 30% water at 20° C. and 10% of an aqueous tanning composition containing 20% of sodium 4-[(4',6'-dichloro-1',3',5'-triazinyl-2')-amino]-benzenesulphonate and buffered with disodium hydrogen phosphate and monosodium dihydrogen phosphate to a pH of 5, is added and drumming is carried on for 60 minutes, then the bath is heated during 120 minutes to 30° C. and drumming is continued overnight at 30-35° C. Then the bath is drained. 300% of water at 20° C. is added and drumming is continued for 30 minutes and then the bath is drained and the leather discharged, horsed up and sammied.

c) Complementary Tanning

After drumming overnight, 1% of cationic surfactant 2-(8-heptadecenyl)-4,5-dihydro-1,3-bis(2-hydroxyethyl)-1H-imidazolium chloride is added and drumming is carried on for 60 minutes. Then 1% of a syntan based on sulphomethylated dihydroxydiphenylsulphone reacted with formaldehyde is added and drumming is continued for 120 minutes at 35° C. Then the bath is drained off. 300% of water at 20° C. and 0.2% of Preventol® WB (a biocide of Bayer, Germany) are added and drumming is continued for 30 minutes. Then the bath is drained off, the leather is discharged, horsed up and sammied. The so obtained leather is then sammied, split and shaved to 1.3-1.4 mm.

d) Retanning, Fat-Liquoring and Dyeing

The sammied, split and shaved leather is given into the drum, 200% of water at 30° C. and then 0.3% of wetting agent ($C_{12-15}$-alkanol ethoxylated with 7 mols of ethylene oxide per mol of alkanol) are added, the drum is switched on and drumming is carried on for 15 minutes and then the bath is drained off. 200% of water at 30° C. and then 4% of Composition (F1) of Example 4 are added and drumming is continued for 30 minutes. 10% of a retanning syntan based on sulphomethylated dihydroxydiphenylsulphone reacted with formaldehyde are added and drumming is carried on for 90 minutes, then the bath is drained off. 200% of water at 25° C. is added and drumming is continued for 5 minutes and then the bath is drained off. 50% of water at 20° C., 15% of Tara (commercial vegetable tanning agent powder, which is an extract of the pods of Caesalpinia Spinosa), 15% of a retanning syntan based on sulphomethylated dihydroxydiphenylsulphone are added and drumming is continued for 90 minutes. 150% of water at 55° C. and 1% of formic acid are added and drumming is carried on for 60 minutes and then the bath is drained off. 200% of water at 25° C. are added and drumming is continued for 5 minutes and then the bath is drained off. 30% of water at 20° C. and 3% of the black dye C.I. Acid Black 210 are added and drumming is continued for 60 minutes, then 100% of water at 55° C. is added and drumming is continued for 10 minutes, then 7% of Composition (F1) of Example 4 is added and drumming is continued for 60 minutes, then 1% of formic acid is added and drumming is carried on for 10 minutes, then further 2% of formic acid is added and drumming is carried on for 40 minutes then the bath is drained off. 200% of water at 25° C. is added and drumming is carried on for 10 minutes, then the bath is drained off and the leather is discharged, sammied, vacuum dried at 70° C. during 3 minutes, dried hanging, staked and conditioned.

There is obtained a fat-liquored, black dyed leather of satisfactory properties, in particular penetration, tensile properties, feel, hydrophilicity, vapour permeability, fastnesses and substantially non-fogging.

In the same way as fat-liquoring composition (F1) of Example 4, fat-liquoring compositions (F2), (F3), (F4), (F5), (F6), (F7), (F8), (F9) and (F10) of examples 5, 6, 12, 13, 14, 16, 18, 20 and 22 are employed in Application Examples A and B giving fat-liquored, black dyed leathers of satisfactory properties, in particular penetration, tensile properties, feel, hydrophilicity, vapour permeability, fastnesses and substantially non-fogging.

What is claimed is:

1. A process for the production of fat-liquored, tanned leather or pelt, comprising the steps of fat-liquoring and tanning, wherein an animal hide, skin or pelt is fat-liquored with a substituted acylaminopolyorganosiloxane (A) in the presence of a surfactant or surfactant mixture (B), which is an anionic or non-ionic surfactant or mixture of anionic or/and non-ionic surfactants, before, during or/and after tanning, wherein said substituted acylaminopolyorganosiloxane (A) which is a polyorganosiloxane containing substituted acylamino groups linked to silicon atoms of the polysiloxane skeleton via alkylene bridges or mono- or oligo-[alkylene-amino or alkylene-(substituted acyl)amino]- alkylene bridges, wherein alkylene contains 2-4 carbon atoms and the substituted acylamino groups are at least in part of formula

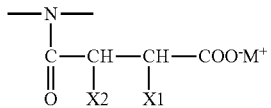 (I)

and for the remaining part are selected from substituted acylamino groups of the formulae

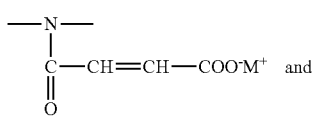 (II)

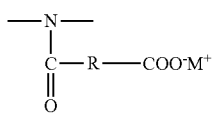 (III)

wherein
X1 signifies hydrogen or the group —SO$_3^-$M$^+$,
X2 signifies hydrogen or the group —SO$_3^-$M$^+$,
  with the proviso that one of X1 and X2 is —SO$_3^-$M$^+$ and the other is hydrogen,
R signifies C$_{2-6}$-alkylene or cyclohexylene,
and
M$^+$ signifies an alkali metal or ammonium cation.

2. The process according to claim 1, wherein the substituted acylaminopolyorganosiloxane (A) is a polyorganosiloxane containing recurring dimethylsiloxy units and units of formula

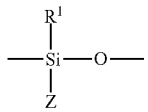 (XIX)

wherein
R$^1$ signifies methyl or methoxy,
Z is a radical of formula

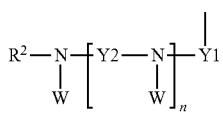 (XX)

R$^2$ signifies hydrogen or C$_{1-4}$-alkyl,
Y1 signifies 1,2- or 1,3-propylene or 2-methyl-1,3-propylene,
Y2 signifies ethylene or propylene,
n signifies 0, 1 or 2, and
W independently signifies hydrogen or a group selected from the groups of formulae

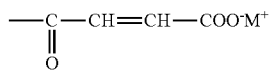 (XII)

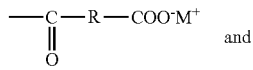 and (XIII)

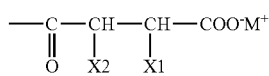 (XXI)

wherein
X1 signifies hydrogen or the group —SO$_3^-$M$^+$,
X2 signifies hydrogen or the group —SO$_3^-$M$^+$,
  with the proviso that one of X1 and X2 is —SO$_3^-$M$^+$ and the other is hydrogen,
R signifies C$_{2-6}$-alkylene or cyclohexylene,
and
M$^+$ signifies an alkali metal or ammonium cation,
with the proviso that at least one of the n+1 symbols W signifies a group of formula (XXI).

3. The process according to claim 2 wherein the substituted acylaminopolysiloxane (A) further contains units of formula

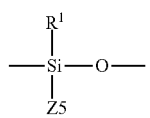 (XXIV)

wherein Z5 is a radical of formula

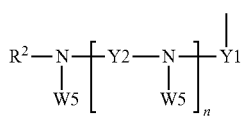 (XXV)

and
R$^1$ signifies methyl or methoxy,
R$^2$ signifies hydrogen or C$_{1-4}$-alkyl,
Y1 signifies 1,2- or 1,3-propylene or 2-methyl-1,3-propylene,
Y2 signifies ethylene or propylene,
n signifies 0, 1 or 2, and
W5 independently signifies hydrogen or a group selected from the groups of formulae (XII) or (XIII)

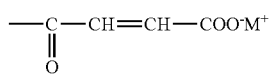 (XII)

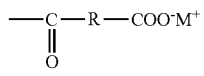 (XIII)

wherein
R signifies C$_{2-6}$-alkylene or cyclohexylene,
and
M$^+$ signifies an alkali metal or ammonium cation.

4. The process according to claim 3 wherein the substituted acylaminopolysiloxane (A) corresponds to the general average statistic formula (XXVI)

$$R^3-\underset{\underset{CH_3}{|}}{\overset{\overset{CH_3}{|}}{Si}}-O-\left[\underset{\underset{Z}{|}}{\overset{\overset{R^1}{|}}{Si}}-O\right]_m-\left[\underset{\underset{Z5}{|}}{\overset{\overset{R^1}{|}}{Si}}-O\right]_{p3}-\underset{\underset{CH_3}{|}}{\overset{\overset{CH_3}{|}}{Si}}-R^3$$

wherein
$R^3$ signifies methyl, methoxy or hydroxy,
m signifies 20 to 400,
p3 signifies 1 to 15,
p4 signifies 0 to (4*p3),
(p3+p4)=p,
p signifies 1-60
Z5 has the meaning as specified in claim 3
and the ratio of m/p is in the range of 4-70.

5. The process according to claim 4, wherein the substituted acylaminopolysiloxane (A) is of the general average statistic formula (XXVII)

$$R^3-\underset{\underset{CH_3}{|}}{\overset{\overset{CH_3}{|}}{Si}}-O-\left[\underset{\underset{Z3}{|}}{\overset{\overset{R^1}{|}}{Si}}-O\right]_m-\left[\underset{\underset{Z4}{|}}{\overset{\overset{R^1}{|}}{Si}}-O\right]_{p5}-\left[\underset{\underset{Z5}{|}}{\overset{\overset{R^1}{|}}{Si}}-O\right]_{p6}-\underset{\underset{CH_3}{|}}{\overset{\overset{CH_3}{|}}{Si}}-R^3$$

wherein
Z3 is a radical of formula (XXII)

$$R^2-N-\left[-Y2-N-\right]-Y1$$
$$\underset{\underset{\underset{X2\ X1}{|\ |}}{CH-CH-COO^-M^+}}{\overset{C=O}{|}}\quad\underset{\underset{\underset{X2\ X1}{|\ |}}{CH-CH-COO^-M^+}}{\overset{C=O}{|}}$$

Z4 is a radical of formula (XXIII)

$$R^2-N-\left[-Y2-N-\right]_{n1}-Y1$$
$$\quad\ \ \underset{W4}{|}\quad\quad\quad\underset{W4}{|}$$

wherein
n1 signifies 1 or 2
W4 independently signifies hydrogen or a group selected from the groups of formulae (XII) or (XIII) or (XXI) defined as follows (XII)
$$-\underset{\underset{O}{\|}}{C}-CH=CH-COO^-M^+$$

(XIII)
$$-\underset{\underset{O}{\|}}{C}-R-COO^-M^+\quad \text{and}$$

(XXI)
$$-\underset{\underset{O}{\|}}{C}-\underset{\underset{X2}{|}}{CH}-\underset{\underset{X1}{|}}{CH}-COO^-M^+$$

at least one of the n1+1 symbols W4 signifying a group of formula (XXI) and at least one signifying hydrogen or a group of formula (XII) or (XIII),
p5 signifies 0 to 15,
p6 signifies 0 to 14,
(p5+p6)=p3
and
(p4+p5+p6)=p,
and the symbols X1, X2, M⁺, R¹, R², R, Y1, Y2, Z5, R³, m, p3 and p4 have the significances stated in claim 4.

6. The process according to claim 1, wherein (B) is an anionic or non-ionic surfactant or surfactant mixture selected from:
(B1) $C_{9-24}$-aliphatic alcohol oligo or poly($C_{2-3}$-alkylene) glycolethers, $C_{9-24}$-aliphatic carboxylic acids oligo or poly($C_{2-3}$-alkylene)glycolesters,
(B2) mono- and/or diesters of maleic, fumaric or succinic acid with $C_{9-24}$-aliphatic alcohol oligo or poly($C_{2-3}$-alkylene)glycolethers or with $C_{9-24}$-aliphatic carboxylic acids oligo or poly($C_{2-3}$-alkylene)glycolesters,
(B3) sulphonated (sulphited) mono- and/or diesters of maleic or fumaric acid with $C_{9-24}$-aliphatic alcohol oligo or poly($C_{2-3}$-alkylene) glycolethers or of $C_{9-24}$-aliphatic carboxylic acids oligo or poly($C_{2-3}$-alkylene) glycolesters,
(B4) $C_{9-24}$-aliphatic alcohol oligo or poly($C_{2-3}$-alkylene) glycolether phosphates or $C_{9-24}$-aliphatic carboxylic acid oligo or poly($C_{2-3}$-alkylene)glycolester phosphates,
(B5) $C_{9-24}$-aliphatic sulphonates, $C_{4-18}$-alkylbenzene sulphonates,
(B6) $C_{9-24}$-fatty acid sarcosides,
(B7) glycerol or sorbitan mono- and/or diesters of $C_{9-24}$-aliphatic carboxylic acids,
(B8) maleic, fumaric or succinic acid mono-$C_{9-24}$-aliphatic amides,
(B9) sulphonated (sulphited) derivatives of maleic or fumaric acid mono-$C_{9-24}$-aliphatic amides,
and mixtures of two or more thereof.

7. The process according to claim 1, wherein substituted acylaminopolysiloxane (A) is the reaction product of an acylaminopolysiloxane ($S_A$), which is a polyorganosiloxane containing substituted acylamino groups linked to silicon atoms of the polysiloxane skeleton via alkylene bridges or mono- or oligo-[alkylene-amino or alkylene-(substituted acyl)amino]-alkylene bridges and wherein the substituted acylamino groups are of formula (II) or of formulae (II) and (III), with a sulphiting reactant.

8. The process according to claim 7, wherein acylaminopolysiloxane ($S_A$) is the reaction product of an aminopolysiloxane (S) containing primary and/or secondary amino groups which are bonded to silicon atoms of the polysiloxane skeleton via alkylene bridges or mono- or oligo-(alkyleneamino)-alkylene bridges, with (1) butenedioic acid anhydride or monochloride
and optionally
(2) the anhydride or monochloride of a $C_{4-8}$-alkanedioic acid or cyclohexylenedicarboxylic acid
to give an acylaminopolyorganosiloxane ($S_A$) containing substituted amide groups of formula (II) and optionally (III).

9. The process according to claim 1, wherein the substituted acylaminopolysiloxane (A) is employed in the form of an aqueous composition (F).

10. The process according to claim 9, wherein aqueous composition (F) comprises the substituted acylaminopolysiloxane (A) and a surfactant or surfactant mixture (B).

11. The process according to claim 9, wherein aqueous composition (F) further comprises
(C) one or more formulation additives
and/or
(D) an agent to protect against the damaging action of microorganisms.

12. The process according to claim 1, wherein an organic fat-liquoring agent (G) is also employed.

13. The process according to claim 1 wherein tanning is carried out with a heterocyclic tanning agent.

14. The process according to claim 13 wherein after tanning with a heterocyclic tanning agent a complementary tanning is carried out.

15. The process according to claim 13, wherein the substituted acylaminopolysiloxane (A) is employed in the form of an aqueous composition (F).

16. The process according to claim 13, wherein an aqueous composition (F), is employed for retanning.

17. The process according to claim 16, wherein the aqueous composition (F), comprising a surfactant (B3) or a mixture of a surfactant (B3) and a surfactant (B2) and/or (B6) is employed for retanning, wherein
said (B2) is selected from the group consisting of mono- and/or diesters of maleic, fumaric or succinic acid with $C_{9-24}$-aliphatic alcohol oligo or poly($C_{2-3}$-alkylene)glycolethers or with $C_{9-24}$-aliphatic carboxylic acids oligo or poly($C_{2-3}$-alkylene)glycolesters;
said (B3) is selected from the group consisting of sulphonated (sulphited) mono- and/or diesters of maleic or fumaric acid with $C_{9-24}$-aliphatic alcohol oligo or poly($C_{2-3}$-alkylene) glycolethers or of $C_{9-24}$-aliphatic carboxylic acids oligo or poly($C_{2-3}$-alkylene)glycolesters; and
said (B6) is selected from the group consisting of $C_{9-24}$-fatty acid sarcosides.

18. A tanned pelt or leather fat-liquored with the substituted acylaminopolysiloxane (A) in the presence of the surfactant or surfactant mixture (B) according to claim 1.

19. The tanned pelt or leather according to claim 18, being further processed by dyeing and finishing.

20. The tanned pelt or leather according to claim 19 being retanned before the fat-liquoring with the substituted acylaminopolysiloxane (A).

21. The tanned pelt or leather according to claim 20, being dyed before the fat-liquoring with (A).

22. A substituted acylaminopolysiloxane (A') which is a polyorganosiloxane containing substituted acylamino groups linked to silicon atoms of the polysiloxane skeleton via mono- or oligo-[alkylene-amino or alkylene-(substituted acyl)amino]-alkylene bridges, wherein alkylene contains 2-4 carbon atoms and the substituted acylamino groups are at least in part of formula (I), and for the remaining part are selected from substituted acylamino groups of formula (II) and (III)

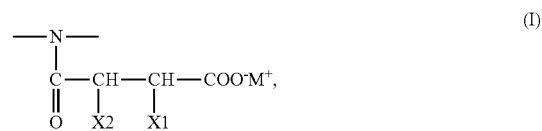

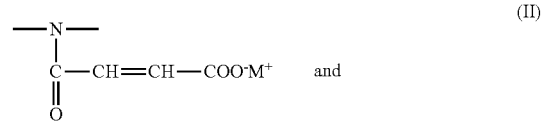

wherein
X1 signifies hydrogen or the group $-SO_3^-M^+$,
X2 signifies hydrogen or the group $-SO_3^-M^+$,
with the proviso that one of X1 and X2 is $-SO_3^-M^+$ and the other is hydrogen,
R signifies $C_{2-6}$-alkylene or cyclohexylene,
and
$M^+$ signifies an alkali metal or ammonium cation.

23. The substituted acylaminopolysiloxane (A') according to claim 22, wherein the acylaminopolysiloxane is a polyorganosiloxane containing recurring dimethylsiloxy units and units of formula (XIX) with the proviso that n signifies 1 or 2, wherein the formula (XIX) is defined as follows:

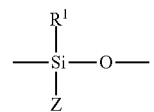

wherein
$R^1$ signifies methyl or methoxy,
Z is a radical of formula

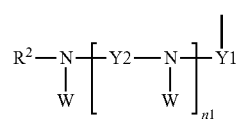

$R^2$ signifies hydrogen or $C_{1-4}$-alkyl,
Y1 signifies 1,2- or 1,3-propylene or 2-methyl-1,3-propylene,
Y2 signifies ethylene or propylene,
n signifies 1 or 2, and
W independently signifies hydrogen or a group selected from the groups of formulae

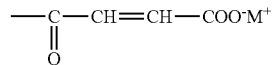

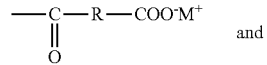

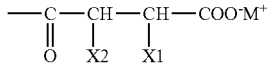

with the proviso that at least one of the n+1 symbols W signifies a group of formula (XXI)

wherein

X1 signifies hydrogen or the group —SO$_3^-$M$^+$,

X2 signifies hydrogen or the group —SO$_3^-$M$^+$,
    with the proviso that one of X1 and X2 is —SO$_3^-$M$^+$ and the other is hydrogen, R signifies C$_{2-6}$-alkylene or cyclohexylene, and M$^+$ signifies an alkali metal or ammonium cation.

24. The substituted acylaminopolysiloxane (A') according to claim 23 further containing units of formula (XXIV) with the proviso that n signifies 1 or 2, wherein the formula (XXIV) is defined as follows:

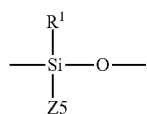
(XXIV)

wherein Z5 is a radical of formula

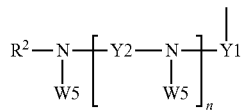
(XXV)

wherein

R$^1$ signifies methyl or methoxy,

R$^2$ signifies hydrogen or C$_{1-4}$-alkyl,

Y1 signifies 1,2- or 1,3-propylene or 2-methyl-1,3-propylene,

Y2 signifies ethylene or propylene, n signifies 1 or 2, and

W5 independently signifies hydrogen or a group selected from the groups of formulae (XII) or (XIII),

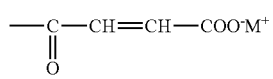
(XII)

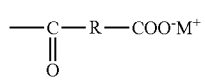
(XIII)

wherein

X1 signifies hydrogen or the group —SO$_3^-$M$^+$,

X2 signifies hydrogen or the group —SO$_3^-$M$^+$,
    with the proviso that one of X1 and X2 is —SO$_3^-$M$^+$ and the other is hydrogen, R signifies C$_{2-6}$-alkylene or cyclohexylene, and M$^+$ signifies an alkali metal or ammonium cation.

25. The substituted acylaminopolysiloxane (A') according to claim 24 of the general average statistic formula (XXVI) with the proviso that in Z and in Z5 n signifies 1 or 2, wherein the formula (XXVI) is defined as follows:

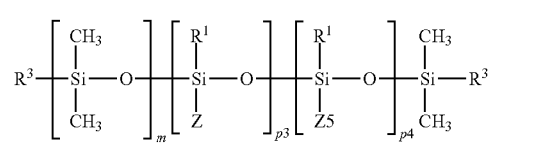
(XXVI)

wherein

R$^3$ signifies methyl, methoxy or hydroxy, m signifies 20 to 400, p3 signifies 1 to 15, p4 signifies 0 to (4*p3), (p3+p4)=p, p signifies 1-60

Z5 has the meaning as specified in claim 24 and the ratio of m/p is in the range of 4-70.

26. The substituted acylaminopolysiloxane (A') according to claim 25 of the general average statistic formula (XXVII) with the proviso that n signifies 1 or 2, wherein the formula (XXVII) is defined as follows:

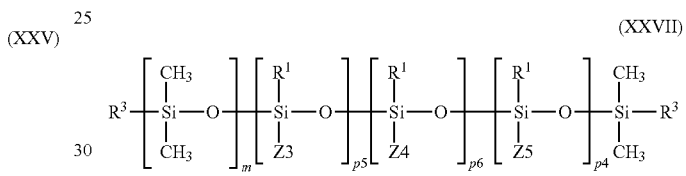
(XXVII)

wherein

Z3 is a radical of formula

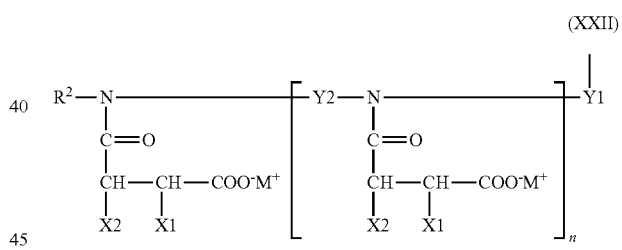
(XXII)

Z4 is a radical of formula

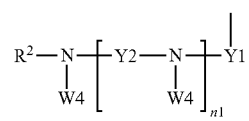
(XXIII)

wherein n1 signifies 1 or 2

W4 independently signifies hydrogen or a group selected from the groups of formulae (XII) or (XIII) or (XXI) which are defined as follows:

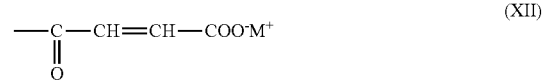
(XII)

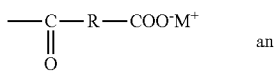 (XIII)

and

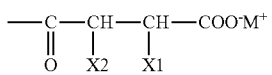 (XXI)

wherein

R signifies $C_{2-6}$-alkylene or cyclohexylene, at least one of the n1+1 symbols W4 signifying a group of formula (XXI) and at least one signifying hydrogen or a group of formula (XII) or (XIII), p5 signifies 0 to 15, p6 signifies 0 to 14, (p5±p6)=p3 and (p4+p5+p6)=p, and the symbols X1, X2, M$^+$, R$^1$, R$^2$, Y1, Y2, Z5, R$^3$, m, p3 and p4 have the significances stated in claim 25.

27. A process for the production of acylaminopolysiloxanes (A') according to claim 22, the process comprising:

reacting, with a sulphiting reactant, an acylaminopolysiloxane (SA) which is a polyorganosiloxane containing substituted acylamino groups linked to silicon atoms of the polysiloxane skeleton via mono- or oligo-[alkyleneamino or alkylene-(substituted acyl)amino]-alkylene bridges and wherein the substituted acylamino groups are of formula (II) or of formulae (II) and (III) defined in claim 22.

28. The process according to claim 27 for the production of acylaminopolysiloxanes (A'), wherein the process further comprises:

reacting an aminopolysiloxane (S') containing primary and/or secondary amino groups which are bonded to silicon atoms of the polysiloxane skeleton via mono- or oligo-(alkyleneamino)-alkylene bridges with (1) butenedioic acid anhydride or monochloride and optionally (2) the anhydride or monochloride of a $C_{4-8}$-alkanedioic acid or cyclohexylenedicarboxylic acid to give the acylaminopolyorganosiloxane ($S_A'$) containing substituted amide groups of formula (II) and optionally (III), and the ($S_A'$) is reacted with the sulphiting reactant.

29. A substituted acylaminopolysiloxane (A') obtainable by the process according to claim 27.

30. A process according to claim 27, which is carried out in the presence of (B) an anionic or non-ionic surfactant or mixture of anionic or/and non-ionic surfactants.

31. An aqueous composition (F') comprising the substituted acylaminopolysiloxane (A') according to claim 22.

32. The aqueous composition (F') according to claim 31 further comprising a surfactant or surfactant mixture (B).

33. The aqueous composition (F') according to claim 31 further comprising (C) one or more formulation additives and/or (D) an agent to protect against the damaging action of microorganisms.

* * * * *

UNITED STATES PATENT AND TRADEMARK OFFICE
CERTIFICATE OF CORRECTION

PATENT NO.  : 9,447,477 B2
APPLICATION NO. : 14/374867
DATED : September 20, 2016
INVENTOR(S) : Gamarino et al.

It is certified that error appears in the above-identified patent and that said Letters Patent is hereby corrected as shown below:

In the Specification

In Column 10 at Line 29, Change "(XVIII" to --(XVIII)--.

In Column 14 at Line 10, Change "OWN" to --O/W--.

In Column 14 at Line 58, Change "ethylenoxy" to --ethyleneoxy--.

In Column 14 at Line 59, Change "ethylenoxy" to --ethyleneoxy--.

In Column 17 at Line 46, Change "(A)." to --(A').--.

In Column 17 at Line 67, Change "(S)" to --(S')--.

In Column 18 at Line 22, Change "(A)" to --(A')--.

In Column 19 at Line 28, Change "ten," to --teri,--.

In Column 24 at Line 43, Change "3-[(2-aminoethyl)" to --3[(2-aminoethyl)--.

In Column 24 at Line 44, Change "3-[(2-aminoethyl)" to --3[(2-aminoethyl)--.

In Column 26 at Line 9, After "40.0%)" insert --.--.

In Column 26 at Line 14 (approx.), Change "Cylaminosilicone" to --Acylaminosilicone--.

In Column 27 at Line 39, Change "62.8%." to --62.8%,--.

Signed and Sealed this
Seventh Day of February, 2017

Michelle K. Lee
*Director of the United States Patent and Trademark Office*

CERTIFICATE OF CORRECTION (continued)

In the Claims

In Column 36 at Line 36, In Claim 6, change "poly($C_{2-3}$-alkylene) glycolethers" to --poly($C_{2-3}$ alkylene)glycolethers--.

In Column 37 at Line 44, In Claim 17, change "($C_{2-3}$-alkylene) glycolethers" to --($C_{2-3}$ alkylene)glycolethers--.

In Column 37 at Line 54, In Claim 20, change "claim 19" to --claim 19,--.

In Column 38 at Lines 41-46, In Claim 23, change " 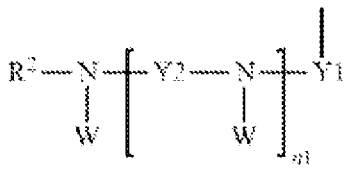 " to

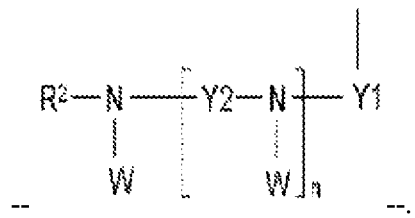
--.

In Column 41 at Line 18 (approx.), In Claim 26, change "(p5±p6)=p3" to --(p5+p6)=p3--.

In Column 41 at Line 25 (approx.), In Claim 27, change "(SA)" to --($S_A'$)--.